(12) United States Patent
Burkhard et al.

(10) Patent No.: US 10,245,318 B2
(45) Date of Patent: Apr. 2, 2019

(54) FLAGELLIN-CONTAINING PROTEIN NANOPARTICLES AS A VACCINE PLATFORM

(71) Applicant: ALPHA-O PEPTIDES AG, Riehen (CH)

(72) Inventors: Peter Burkhard, Mansfield Center, CT (US); Senthil Kumar Raman, Basel (CH); Sara Maria Paulillo, Basel (CH); Matteo Piazza, Basel (CH); Caroline Kulangara, Basel (CH); Christian Mittelholzer, Kaiseraugst (CH)

(73) Assignee: ALPHA-O PEPTIDES AG, Riehen (CH)

( * ) Notice: Subject to any disclaimer, the term of this patent is extended or adjusted under 35 U.S.C. 154(b) by 0 days.

(21) Appl. No.: 15/110,449

(22) PCT Filed: Jan. 9, 2015

(86) PCT No.: PCT/EP2015/050289
§ 371 (c)(1),
(2) Date: Jul. 8, 2016

(87) PCT Pub. No.: WO2015/104352
PCT Pub. Date: Jul. 16, 2015

(65) Prior Publication Data
US 2016/0324958 A1    Nov. 10, 2016

(30) Foreign Application Priority Data

Jan. 9, 2014 (EP) ..................................... 14150600
Oct. 16, 2014 (EP) ..................................... 14189264

(51) Int. Cl.
| | | |
|---|---|---|
| A61K 39/39 | (2006.01) | |
| A61K 39/00 | (2006.01) | |
| A61K 39/015 | (2006.01) | |
| C07K 14/195 | (2006.01) | |

(52) U.S. Cl.
CPC .......... *A61K 39/39* (2013.01); *A61K 39/0013* (2013.01); *A61K 39/015* (2013.01); *C07K 14/195* (2013.01); *A61K 2039/55555* (2013.01); *A61K 2039/6068* (2013.01); *A61K 2039/64* (2013.01)

(58) Field of Classification Search
None
See application file for complete search history.

(56) References Cited

U.S. PATENT DOCUMENTS

| | | | | |
|---|---|---|---|---|
| 8,546,337 B2 * | 10/2013 | Burkhard | ............. | A61K 39/145 424/184.1 |
| 2011/0020378 A1 * | 1/2011 | Burkhard | ............. | A61K 39/145 424/184.1 |

FOREIGN PATENT DOCUMENTS

WO    2013/144579    10/2013

OTHER PUBLICATIONS

International Search Report dated Mar. 23, 2015 in International Application No. PCT/EP2015/050289.
Liu et al., "Immunogenicity and Efficacy of Flagellin-Fused Vaccine Candidates Targeting 2009 Pandemic H1N1 Influenza in Mice", PLOS ONE, vol. 6, No. 6, Jun. 6, 2011, XP002725576. pp. 1-9.
Yang et al., "Antigen replacement of domains D2 and D3 in flagellin promotes mucosal IgA production and attenuates flagellin-induced inflammatory response after intranasal immunization", Human Vaccines & Immunotherapeutics, vol. 9, No. 5, May 2013, pp. 1084-1092, XP002725577.
Mizel et al., "Flagellin as an Adjuvant: Cellular Mechanisms and Potential", The Journal of Immunology, vol. 185, No. 10, Nov. 15, 2010, pp. 5677-5682, XP055066659.
Salman et at, "Immunoadjuvant capacity of flagellin and mannosamine-coated poly(anhyride) nanoparticles in oral vaccination", Vaccine, vol. 27, No. 35, Jul. 2009, pp. 4784-4790, XP002725578.

* cited by examiner

*Primary Examiner* — James H Alstrum-Acevedo
*Assistant Examiner* — Tara L Martinez
(74) *Attorney, Agent, or Firm* — Wenderoth, Lind & Ponack, L.L.P.

(57) ABSTRACT

The present invention relates to self-assembling protein nanoparticles constructed from suitable oligomerization domains and further incorporating the TLR5 binding protein flagellin as an adjuvant molecule. Furthermore, the invention relates to the use of such nanoparticles for vaccination.

13 Claims, 14 Drawing Sheets
Specification includes a Sequence Listing.

A

B

SEQUENCE LISTING

```
<160> NUMBER OF SEQ ID NOS: 32

<210> SEQ ID NO 1
<211> LENGTH: 11
<212> TYPE: PRT
<213> ORGANISM: Artificial sequence
<220> FEATURE:
<223> OTHER INFORMATION: Synthetic construct

<400> SEQUENCE: 1

Lys Tyr Lys Asp Gly Asp Lys Gly Asp Asp Lys
1               5                   10

<210> SEQ ID NO 2
<211> LENGTH: 11
<212> TYPE: PRT
<213> ORGANISM: Artificial sequence
<220> FEATURE:
<223> OTHER INFORMATION: Synthetic construct

<400> SEQUENCE: 2

Lys Leu Lys Leu Leu Leu Leu Leu Lys Leu Lys
1               5                   10

<210> SEQ ID NO 3
<211> LENGTH: 27
<212> TYPE: PRT
<213> ORGANISM: Artificial sequence
<220> FEATURE:
<223> OTHER INFORMATION: Synthetic construct

<400> SEQUENCE: 3
```

Gly Tyr Ile Pro Glu Ala Pro Arg Asp Gly Gln Ala Tyr Val Arg Lys
1               5                   10                  15

Asp Gly Glu Trp Val Leu Leu Ser Thr Phe Leu
            20                  25

<210> SEQ ID NO 4
<211> LENGTH: 392
<212> TYPE: PRT
<213> ORGANISM: Artificial sequence
<220> FEATURE:
<223> OTHER INFORMATION: Synthetic construct

<400> SEQUENCE: 4

Met Gly His His His His His Ala Ser Trp Arg Trp Asp Gly Gly
1               5                   10                  15

Leu Val Pro Arg Gly Ser Trp Gln Thr Trp Asn Ala Arg Trp Asp Gln
                20                  25                  30

Trp Ser Asn Asp Trp Asn Ala Trp Arg Ser Asp Trp Gln Ala Trp Arg
            35                  40                  45

Asp Asp Trp Ala Arg Trp Arg Ala Leu Trp Met Gly Gly Arg Leu Leu
        50                  55                  60

Leu Arg Leu Glu Glu Leu Glu Arg Leu Glu Glu Leu Glu Arg Arg
65                  70                  75                  80

Leu Glu Glu Leu Glu Arg Phe Val Ala Ala Trp Thr Leu Arg Val Arg
                85                  90                  95

Ala Leu Glu Arg Arg Leu Glu Glu Leu Glu Arg Arg Ile Glu Glu Ile
                100                 105                 110

Ala Arg Gly Met Ala Gln Val Ile Asn Thr Asn Ser Leu Ser Leu Leu
            115                 120                 125

Thr Gln Asn Asn Leu Asn Lys Ser Gln Ser Ala Leu Gly Thr Ala Ile
130                 135                 140

Glu Arg Leu Ser Ser Gly Leu Arg Ile Asn Ser Ala Lys Asp Asp Ala
145                 150                 155                 160

Ala Gly Gln Ala Ile Ala Asn Arg Phe Thr Ala Asn Ile Lys Gly Leu
                165                 170                 175

Thr Gln Ala Ser Arg Asn Ala Asn Asp Gly Ile Ser Ile Ala Gln Thr
            180                 185                 190

Thr Glu Gly Ala Leu Asn Glu Ile Asn Asn Asn Leu Gln Arg Val Arg
        195                 200                 205

Glu Leu Ala Val Gln Ser Ala Asn Ser Thr Asn Ser Gln Ser Asp Leu
210                 215                 220

Asp Ser Ile Gln Ala Glu Ile Thr Gln Arg Leu Asn Glu Ile Asp Arg
225                 230                 235                 240

Val Ser Gly Gln Thr Gln Phe Asn Gly Val Lys Val Leu Ala Gln Asp
                245                 250                 255

Asn Thr Leu Thr Ile Gln Val Gly Ala Asn Asp Gly Glu Thr Ile Asp
            260                 265                 270

Ile Asp Leu Lys Gln Ile Asn Ser Gln Thr Leu Gly Leu Asp Ser Leu
        275                 280                 285

Asn Val His Gly Ala Pro Val Asp Pro Ala Ser Pro Trp Thr Glu Asn
    290                 295                 300

Pro Leu Gln Lys Ile Asp Ala Ala Leu Ala Gln Val Asp Ala Leu Arg
305                 310                 315                 320

Ser Asp Leu Gly Ala Val Gln Asn Arg Phe Asn Ser Ala Ile Thr Asn
                325                 330                 335

Leu Gly Asn Thr Val Asn Asn Leu Ser Glu Ala Arg Ser Arg Ile Glu
                340                 345                 350

Asp Ser Asp Tyr Ala Thr Glu Val Ser Asn Met Ser Arg Ala Gln Ile
            355                 360                 365

Leu Gln Gln Ala Gly Thr Ser Val Leu Ala Gln Ala Asn Gln Val Pro
        370                 375                 380

Gln Asn Val Leu Ser Leu Leu Arg
385                 390

<210> SEQ ID NO 5
<211> LENGTH: 155
<212> TYPE: PRT
<213> ORGANISM: Artificial sequence
<220> FEATURE:
<223> OTHER INFORMATION: Synthetic construct

<400> SEQUENCE: 5

Met Gly His His His His His Ala Ser Glu Tyr Leu Asn Lys Ile
1               5                   10                  15

Gln Asn Ser Leu Ser Thr Glu Trp Ser Pro Ser Ser Val Thr Gly Ser
            20                  25                  30

Trp Gln Thr Trp Asn Ala Arg Trp Asp Gln Trp Ser Asn Asp Trp Asn
        35                  40                  45

Ala Trp Arg Ser Asp Trp Gln Ala Trp Arg Asp Asp Trp Ala Arg Trp
    50                  55                  60

Arg Ala Leu Trp Met Gly Gly Arg Leu Leu Leu Arg Leu Glu Glu Leu
65                  70                  75                  80

Glu Arg Arg Leu Glu Glu Leu Glu Arg Leu Glu Glu Leu Glu Arg
                85                  90                  95

Phe Val Ala Ala Trp Thr Leu Arg Val Arg Ala Leu Gly Arg Arg Leu
                100                 105                 110

Glu Glu Leu Glu Arg Arg Ile Glu Glu Ile Ala Arg Gly Ser Gly Asp
            115                 120                 125

Pro Asn Ala Asn Pro Asn Val Asp Pro Asn Ala Asn Pro Asn Val Asn
        130                 135                 140

Ala Asn Pro Asn Ala Asn Pro Asn Ala Asn Pro
145                 150                 155

<210> SEQ ID NO 6
<211> LENGTH: 22
<212> TYPE: PRT
<213> ORGANISM: Artificial sequence
<220> FEATURE:
<223> OTHER INFORMATION: Synthetic construct

<400> SEQUENCE: 6

Met Gly His His His His His Ala Ser Trp Arg Trp Asp Gly Gly
1               5                   10                  15

Leu Val Pro Arg Gly Ser
            20

<210> SEQ ID NO 7
<211> LENGTH: 37
<212> TYPE: PRT
<213> ORGANISM: Artificial sequence
<220> FEATURE:
<223> OTHER INFORMATION: Synthetic construct

<400> SEQUENCE: 7

Trp Gln Thr Trp Asn Ala Arg Trp Asp Gln Trp Ser Asn Asp Trp Asn

```
                1               5                   10                  15
Ala Trp Arg Ser Asp Trp Gln Ala Trp Arg Asp Asp Trp Ala Arg Trp
                20                  25                  30

Arg Ala Leu Trp Met
            35

<210> SEQ ID NO 8
<211> LENGTH: 54
<212> TYPE: PRT
<213> ORGANISM: Artificial sequence
<220> FEATURE:
<223> OTHER INFORMATION: Synthetic construct

<400> SEQUENCE: 8

Arg Leu Leu Leu Arg Leu Glu Glu Leu Glu Arg Arg Leu Glu Glu Leu
1               5                   10                  15

Glu Arg Arg Leu Glu Glu Leu Glu Arg Phe Val Ala Ala Trp Thr Leu
                20                  25                  30

Arg Val Arg Ala Leu Glu Arg Arg Leu Glu Glu Leu Glu Arg Arg Ile
            35                  40                  45

Glu Glu Ile Ala Arg Gly
        50

<210> SEQ ID NO 9
<211> LENGTH: 277
<212> TYPE: PRT
<213> ORGANISM: Artificial sequence
<220> FEATURE:
<223> OTHER INFORMATION: Synthetic construct

<400> SEQUENCE: 9

Met Ala Gln Val Ile Asn Thr Asn Ser Leu Ser Leu Leu Thr Gln Asn
1               5                   10                  15

Asn Leu Asn Lys Ser Gln Ser Ala Leu Gly Thr Ala Ile Glu Arg Leu
                20                  25                  30

Ser Ser Gly Leu Arg Ile Asn Ser Ala Lys Asp Asp Ala Ala Gly Gln
            35                  40                  45

Ala Ile Ala Asn Arg Phe Thr Ala Asn Ile Lys Gly Leu Thr Gln Ala
        50                  55                  60

Ser Arg Asn Ala Asn Asp Gly Ile Ser Ile Ala Gln Thr Thr Glu Gly
65                  70                  75                  80

Ala Leu Asn Glu Ile Asn Asn Asn Leu Gln Arg Val Arg Glu Leu Ala
                85                  90                  95

Val Gln Ser Ala Asn Ser Thr Asn Ser Gln Ser Asp Leu Asp Ser Ile
                100                 105                 110

Gln Ala Glu Ile Thr Gln Arg Leu Asn Glu Ile Asp Arg Val Ser Gly
            115                 120                 125

Gln Thr Gln Phe Asn Gly Val Lys Val Leu Ala Gln Asp Asn Thr Leu
        130                 135                 140

Thr Ile Gln Val Gly Ala Asn Asp Gly Glu Thr Ile Asp Ile Asp Leu
145                 150                 155                 160

Lys Gln Ile Asn Ser Gln Thr Leu Gly Leu Asp Ser Leu Asn Val His
                165                 170                 175

Gly Ala Pro Val Asp Pro Ala Ser Pro Trp Thr Glu Asn Pro Leu Gln
                180                 185                 190

Lys Ile Asp Ala Ala Leu Ala Gln Val Asp Ala Leu Arg Ser Asp Leu
            195                 200                 205
```

```
Gly Ala Val Gln Asn Arg Phe Asn Ser Ala Ile Thr Asn Leu Gly Asn
        210                 215                 220

Thr Val Asn Asn Leu Ser Glu Ala Arg Ser Arg Ile Glu Asp Ser Asp
225                 230                 235                 240

Tyr Ala Thr Glu Val Ser Asn Met Ser Arg Ala Gln Ile Leu Gln Gln
                245                 250                 255

Ala Gly Thr Ser Val Leu Ala Gln Ala Asn Gln Val Pro Gln Asn Val
            260                 265                 270

Leu Ser Leu Leu Arg
        275

<210> SEQ ID NO 10
<211> LENGTH: 32
<212> TYPE: PRT
<213> ORGANISM: Artificial sequence
<220> FEATURE:
<223> OTHER INFORMATION: Synthetic construct

<400> SEQUENCE: 10

Met Gly His His His His His His Ala Ser Glu Tyr Leu Asn Lys Ile
1               5                   10                  15

Gln Asn Ser Leu Ser Thr Glu Trp Ser Pro Ser Ser Val Thr Gly Ser
            20                  25                  30

<210> SEQ ID NO 11
<211> LENGTH: 30
<212> TYPE: PRT
<213> ORGANISM: Artificial sequence
<220> FEATURE:
<223> OTHER INFORMATION: Synthetic construct

<400> SEQUENCE: 11

Ser Gly Asp Pro Asn Ala Asn Pro Asn Val Asp Pro Asn Ala Asn Pro
1               5                   10                  15

Asn Val Asn Ala Asn Pro Asn Ala Asn Pro Asn Ala Asn Pro
            20                  25                  30

<210> SEQ ID NO 12
<211> LENGTH: 53
<212> TYPE: PRT
<213> ORGANISM: Artificial sequence
<220> FEATURE:
<223> OTHER INFORMATION: Synthetic construct

<400> SEQUENCE: 12

Ser Ser Asn Ala Lys Trp Asp Gln Trp Ser Asp Trp Gln Thr Trp
1               5                   10                  15

Asn Ala Lys Trp Asp Gln Trp Ser Asn Asp Trp Asn Ala Trp Arg Ser
            20                  25                  30

Asp Trp Gln Ala Trp Lys Asp Asp Trp Ala Arg Trp Asn Gln Arg Trp
        35                  40                  45

Asp Asn Trp Ala Thr
    50

<210> SEQ ID NO 13
<211> LENGTH: 20
<212> TYPE: PRT
<213> ORGANISM: Artificial sequence
<220> FEATURE:
<223> OTHER INFORMATION: Synthetic construct

<400> SEQUENCE: 13
```

```
Glu Tyr Leu Asn Lys Ile Gln Asn Ser Leu Ser Thr Glu Trp Ser Pro
1               5                   10                  15

Ser Ser Val Thr
            20
```

<210> SEQ ID NO 14
<211> LENGTH: 16
<212> TYPE: PRT
<213> ORGANISM: Artificial sequence
<220> FEATURE:
<223> OTHER INFORMATION: Synthetic construct

<400> SEQUENCE: 14

```
Asp Pro Asn Ala Asn Pro Asn Val Asp Pro Asn Ala Asn Pro Asn Val
1               5                   10                  15
```

<210> SEQ ID NO 15
<211> LENGTH: 368
<212> TYPE: PRT
<213> ORGANISM: Artificial sequence
<220> FEATURE:
<223> OTHER INFORMATION: Synthetic construct

<400> SEQUENCE: 15

```
Met Gly His His His His His His Ala Ser Trp Arg Trp Asp Gly Gly
1               5                   10                  15

Leu Val Pro Arg Gly Ser Trp Gln Thr Trp Asn Ala Arg Trp Asp Gln
            20                  25                  30

Trp Ser Asn Asp Trp Asn Ala Trp Arg Ser Trp Gln Ala Trp Arg
        35                  40                  45

Asp Asp Trp Ala Arg Trp Arg Ala Leu Trp Met Gly Gly Arg Leu Leu
    50                  55                  60

Leu Arg Leu Glu Glu Leu Glu Arg Leu Glu Leu Glu Arg Arg
65                  70                  75                  80

Leu Glu Glu Leu Glu Arg Phe Val Ala Ala Trp Thr Leu Arg Val Arg
                85                  90                  95

Ala Leu Glu Arg Arg Leu Glu Glu Leu Glu Arg Arg Ile Glu Glu Ile
            100                 105                 110

Ala Arg Gly Ser Gly Ser Ser Ala Arg Leu Ser Asp Leu Glu Ala Asn
            115                 120                 125

Asn Ala Val Lys Gly Glu Ser Lys Ile Thr Val Asn Gly Ala Glu Tyr
        130                 135                 140

Thr Ala Asn Ala Thr Gly Asp Lys Ile Thr Leu Ala Gly Lys Thr Met
145                 150                 155                 160

Phe Ile Asp Lys Thr Ala Ser Gly Val Ser Thr Leu Ile Asn Glu Asp
                165                 170                 175

Ala Ala Ala Ala Lys Lys Ser Thr Ala Asn Pro Leu Ala Ser Ile Asp
            180                 185                 190

Ser Ala Leu Ser Lys Val Asp Ala Val Arg Ser Ser Leu Gly Ala Ile
            195                 200                 205

Gln Asn Arg Phe Asp Ser Ala Ile Gly Ser Arg Asn Ala Asn Asp Gly
        210                 215                 220

Ile Ser Ile Ala Gln Thr Thr Glu Gly Ala Leu Asn Glu Ile Asn Asn
225                 230                 235                 240

Asn Leu Gln Arg Val Arg Glu Leu Ser Val Gln Ala Thr Asn Gly Thr
                245                 250                 255

Asn Ser Asp Ser Asp Leu Lys Ser Ile Gln Asp Glu Ile Gln Gln Arg
            260                 265                 270
```

Leu Glu Glu Ile Asp Arg Val Ser Asn Gln Thr Gln Phe Asn Gly Val
            275                 280                 285

Lys Val Leu Ser Gln Asp Asn Gln Met Lys Ile Gln Val Gly Ala Asn
        290                 295                 300

Asp Gly Glu Thr Ile Thr Ile Asp Leu Gln Lys Ile Asp Val Lys Ser
305                 310                 315                 320

Leu Gly Leu Asp Gly Phe Asn Val Asn Gly Pro Lys Glu Ala Thr Val
                325                 330                 335

Gly Asp Leu Lys Ser Ser Phe Lys Asn Val Thr Gly Tyr Asp Thr Tyr
            340                 345                 350

Ala Ala Gly Ala Asp Lys Tyr Arg Val Asp Ile Asn Ser Gly Ala Val
        355                 360                 365

<210> SEQ ID NO 16
<211> LENGTH: 14
<212> TYPE: PRT
<213> ORGANISM: Artificial sequence
<220> FEATURE:
<223> OTHER INFORMATION: Synthetic construct

<400> SEQUENCE: 16

Glu Arg Phe Val Ala Ala Trp Thr Leu Arg Val Arg Ala Leu
1               5                   10

<210> SEQ ID NO 17
<211> LENGTH: 351
<212> TYPE: PRT
<213> ORGANISM: Artificial sequence
<220> FEATURE:
<223> OTHER INFORMATION: Synthetic construct

<400> SEQUENCE: 17

Met Gly His His His His His His Ala Ser Gly Ser Trp Glu Lys Trp
1               5                   10                  15

Asn Ala Lys Trp Asp Glu Trp Lys Asn Asp Trp Asn Asp Trp Arg Arg
            20                  25                  30

Asp Trp Gln Ala Trp Val Asp Asp Trp Ala Tyr Trp Thr Leu Thr Trp
        35                  40                  45

Lys Tyr Gly Glu Leu Tyr Ser Lys Leu Ala Glu Leu Glu Arg Arg Asn
    50                  55                  60

Glu Glu Leu Glu Arg Arg Leu Glu Glu Leu Ala Arg Phe Val Ala Ala
65                  70                  75                  80

Leu Ser Met Arg Leu Ala Glu Leu Glu Arg Arg Asn Glu Glu Leu Ala
                85                  90                  95

Arg Gly Ser Gly Ser Ser Ala Arg Leu Ser Asp Leu Glu Ala Asn Asn
            100                 105                 110

Ala Val Arg Gly Glu Ser Lys Ile Thr Val Asn Gly Ala Glu Tyr Thr
        115                 120                 125

Ala Asn Ala Thr Gly Asp Arg Ile Thr Leu Ala Gly Arg Thr Met Phe
    130                 135                 140

Ile Asp Arg Thr Ala Ser Gly Val Ser Thr Leu Ile Asn Glu Asp Ala
145                 150                 155                 160

Ala Ala Ala Arg Arg Ser Thr Ala Asn Pro Leu Ala Ser Ile Asp Ser
                165                 170                 175

Ala Leu Ser Arg Val Asp Ala Val Arg Ser Ser Leu Gly Ala Ile Gln
            180                 185                 190

Asn Arg Phe Asp Ser Ala Ile Gly Ser Lys Asn Ala Asn Asp Gly Ile

```
            195                 200                 205
Ser Ile Ala Gln Thr Thr Glu Gly Ala Leu Asn Glu Ile Asn Asn Asn
210                 215                 220

Leu Gln Arg Val Arg Glu Leu Ser Val Gln Ala Thr Asn Gly Thr Asn
225                 230                 235                 240

Ser Asp Ser Asp Leu Arg Ser Ile Gln Asp Glu Ile Gln Gln Arg Leu
                    245                 250                 255

Glu Glu Ile Asp Arg Val Ser Asn Gln Thr Gln Phe Asn Gly Val Lys
                260                 265                 270

Val Leu Ser Gln Asp Asn Gln Met Lys Ile Gln Val Gly Ala Lys Asp
            275                 280                 285

Gly Glu Thr Ile Thr Ile Asp Leu Gln Lys Ile Asp Val Lys Ser Leu
        290                 295                 300

Gly Leu Asp Gly Phe Asn Val Asn Gly Pro Arg Glu Ala Thr Val Gly
305                 310                 315                 320

Asp Leu Arg Ser Ser Phe Arg Asn Val Thr Gly Tyr Asp Thr Tyr Ala
                    325                 330                 335

Ala Gly Ala Asp Arg Tyr Arg Val Asp Ile Asn Ser Gly Ala Val
                340                 345                 350

<210> SEQ ID NO 18
<211> LENGTH: 399
<212> TYPE: PRT
<213> ORGANISM: Artificial sequence
<220> FEATURE:
<223> OTHER INFORMATION: Synthetic construct

<400> SEQUENCE: 18

Met Gly His His His His His His Ala Ser Gly Ser Trp Glu Lys Trp
1               5                   10                  15

Asn Ala Lys Trp Asp Glu Trp Lys Asn Asp Trp Asn Asp Trp Arg Arg
                20                  25                  30

Asp Trp Gln Ala Trp Val Asp Asp Trp Ala Tyr Trp Thr Leu Thr Trp
            35                  40                  45

Lys Tyr Gly Glu Leu Tyr Ser Lys Leu Ala Glu Leu Glu Arg Arg Asn
50                  55                  60

Glu Glu Leu Glu Arg Arg Leu Glu Glu Leu Ala Arg Phe Val Ala Ala
65                  70                  75                  80

Leu Ser Met Arg Leu Ala Glu Leu Glu Arg Arg Asn Glu Glu Leu Ala
                85                  90                  95

Arg Gly Ser Gly Ser Thr Val Glu Gln Lys Thr Arg Pro Phe Thr Leu
            100                 105                 110

Pro Asn Leu Pro Leu Ser Ser Leu Ser Asn Ser Arg Ala Pro Leu Pro
        115                 120                 125

Ile Ser Ser Met Gly Ile Ser Pro Asp Asn Val Gln Ser Val Gln Phe
130                 135                 140

Gln Asn Gly Arg Cys Thr Leu Asp Gly Arg Leu Val Gly Thr Thr Pro
145                 150                 155                 160

Val Ser Leu Ser His Val Ala Lys Ile Arg Gly Thr Ser Asn Gly Thr
                165                 170                 175

Val Ile Asn Leu Thr Glu Leu Asp Gly Thr Pro Phe His Pro Phe Glu
            180                 185                 190

Gly Pro Ala Pro Ile Gly Phe Pro Asp Leu Gly Gly Cys Asp Trp His
        195                 200                 205

Ile Asn Met Thr Gln Phe Gly His Ser Ser Gln Thr Gln Tyr Asp Val
```

```
                        210                 215                 220
Asp Thr Thr Pro Asp Thr Phe Val Pro His Leu Gly Ser Ile Gln Ala
225                 230                 235                 240

Asn Gly Ile Gly Ser Gly Asn Tyr Val Gly Val Leu Ser Trp Ile Ser
                245                 250                 255

Pro Pro Ser His Pro Ser Gly Ser Gln Val Asp Leu Trp Lys Ile Pro
            260                 265                 270

Asn Tyr Gly Ser Ser Ile Thr Glu Ala Thr His Leu Ala Pro Ser Val
                275                 280                 285

Tyr Pro Pro Gly Phe Gly Glu Val Leu Val Phe Met Ser Lys Met
        290                 295                 300

Pro Gly Pro Gly Ala Tyr Asn Leu Pro Cys Leu Leu Pro Gln Glu Tyr
305                 310                 315                 320

Ile Ser His Leu Ala Ser Glu Gln Ala Pro Thr Val Gly Glu Ala Ala
                325                 330                 335

Leu Leu His Tyr Val Asp Pro Asp Thr Gly Arg Asn Leu Gly Glu Phe
                340                 345                 350

Lys Ala Tyr Pro Asp Gly Phe Leu Thr Cys Val Pro Asn Gly Ala Ser
                355                 360                 365

Ser Gly Pro Gln Gln Leu Pro Ile Asn Gly Val Phe Val Phe Val Ser
        370                 375                 380

Trp Val Ser Arg Phe Tyr Gln Leu Lys Pro Val Gly Thr Ala Ser
385                 390                 395

<210> SEQ ID NO 19
<211> LENGTH: 360
<212> TYPE: PRT
<213> ORGANISM: Artificial sequence
<220> FEATURE:
<223> OTHER INFORMATION: Synthetic construct

<400> SEQUENCE: 19

Met Gly His His His His His His Ala Ser Trp Lys Trp Asp Gly Gly
1               5                   10                  15

Leu Val Pro Arg Gly Ser Trp Gln Thr Trp Asn Ala Lys Trp Asp Gln
                20                  25                  30

Trp Ser Asn Asp Trp Asn Ala Trp Arg Ser Asp Trp Gln Ala Trp Lys
            35                  40                  45

Asp Asp Trp Ala Arg Trp Arg Ala Leu Trp Met Gly Gly Arg Leu Leu
50                  55                  60

Leu Arg Leu Glu Glu Leu Glu Arg Arg Leu Glu Glu Leu Ala Lys Phe
65                  70                  75                  80

Val Ala Ala Trp Thr Leu Lys Ala Ala Ala Val Asp Leu Glu Leu Ala
                85                  90                  95

Ala Leu Arg Arg Arg Leu Glu Glu Leu Ala Arg Gly Asn Thr Asn Ser
                100                 105                 110

Leu Ser Leu Leu Thr Gln Asn Asn Leu Asn Lys Ser Gln Ser Ala Leu
            115                 120                 125

Gly Thr Ala Ile Glu Arg Leu Ser Ser Gly Leu Arg Ile Asn Ser Ala
130                 135                 140

Lys Asp Asp Ala Ala Gly Gln Ala Ile Ala Asn Arg Phe Thr Ala Asn
145                 150                 155                 160

Ile Lys Gly Leu Thr Gln Ala Ser Arg Asn Ala Asn Asp Gly Ile Ser
                165                 170                 175

Ile Ala Gln Thr Thr Glu Gly Ala Leu Asn Glu Ile Asn Asn Asn Leu
```

```
            180                 185                 190
Gln Arg Val Arg Glu Leu Ala Val Gln Ser Ala Asn Ser Thr Asn Ser
        195                 200                 205

Gln Ser Asp Leu Asp Ser Ile Gln Ala Glu Ile Thr Gln Arg Leu Asn
    210                 215                 220

Glu Ile Asp Arg Val Ser Gly Gln Thr Gln Phe Asn Gly Val Lys Val
225                 230                 235                 240

Leu Ala Gln Asp Asn Thr Leu Thr Ile Gln Val Gly Ala Asn Asp Gly
                245                 250                 255

Glu Thr Ile Asp Ile Asp Leu Lys Gln Ile Asn Ser Gln Thr Leu Gly
            260                 265                 270

Leu Asp Gly Gly Glu Asn Pro Leu Gln Lys Ile Asp Ala Ala Leu Ala
        275                 280                 285

Gln Val Asp Thr Leu Arg Ser Asp Leu Gly Ala Val Gln Asn Arg Phe
    290                 295                 300

Asn Ser Ala Ile Thr Asn Leu Gly Asn Thr Val Asn Asn Leu Thr Ser
305                 310                 315                 320

Val Arg Ser Arg Ile Glu Asp Ser Asp Tyr Ala Thr Glu Val Ser Asn
                325                 330                 335

Met Ser Arg Ala Gln Ile Leu Gln Gln Ala Gly Thr Ser Val Leu Ala
            340                 345                 350

Gln Ala Asn Gln Val Pro Gln Asn
        355                 360

<210> SEQ ID NO 20
<211> LENGTH: 128
<212> TYPE: PRT
<213> ORGANISM: Artificial sequence
<220> FEATURE:
<223> OTHER INFORMATION: Synthetic construct

<400> SEQUENCE: 20

Met Gly His His His His His His Ala Ser Trp Lys Trp Asp Gly Gly
1               5                   10                  15

Leu Val Pro Arg Gly Ser Trp Gln Thr Trp Asn Ala Lys Trp Asp Gln
            20                  25                  30

Trp Ser Asn Asp Trp Asn Ala Trp Arg Ser Asp Trp Gln Ala Trp Lys
        35                  40                  45

Asp Asp Trp Ala Arg Leu Arg Ala Leu Leu Met Gly Gly Arg Leu Leu
    50                  55                  60

Leu Arg Leu Glu Glu Leu Glu Arg Arg Leu Glu Glu Leu Ala Lys Phe
65                  70                  75                  80

Val Ala Ala Trp Thr Leu Lys Ala Ala Ala Val Asp Leu Glu Leu Ala
                85                  90                  95

Ala Leu Arg Arg Arg Leu Glu Glu Leu Ala Arg Gly Gly Ser Gly Ala
            100                 105                 110

Asn Ala Asn Pro Asn Ala Asn Pro Asn Ala Asn Pro Asn Ala Asn Pro
        115                 120                 125

<210> SEQ ID NO 21
<211> LENGTH: 382
<212> TYPE: PRT
<213> ORGANISM: Artificial sequence
<220> FEATURE:
<223> OTHER INFORMATION: Synthetic construct

<400> SEQUENCE: 21
```

```
Met Gly His His His His His His Ala Ser Gly Ser Trp Glu Glu Trp
 1               5                  10                  15

Asn Ala Arg Trp Asp Glu Trp Asn Asp Trp Asn Asp Trp Arg Glu
             20                  25                  30

Asp Trp Gln Ala Trp Arg Asp Asp Trp Ala Arg Trp Arg Ala Thr Trp
             35                  40                  45

Met Gly Gly Arg Leu Leu Ser Arg Leu Glu Arg Leu Glu Arg Arg Asn
 50                  55                  60

Glu Glu Leu Arg Arg Leu Leu Gln Leu Leu Arg Asn Arg Leu Glu Arg
 65                  70                  75                  80

Leu Ala Gln Phe Val Arg Ala Leu Ser Met Gln Asn Ala Glu Leu Glu
                 85                  90                  95

Arg Arg Leu Glu Glu Leu Ala Arg Gly Met Ala Gln Val Ile Asn Thr
             100                 105                 110

Asn Ser Leu Ser Leu Leu Thr Gln Asn Asn Leu Asn Lys Ser Gln Ser
             115                 120                 125

Ala Leu Gly Thr Ala Ile Glu Arg Leu Ser Ser Gly Leu Arg Ile Asn
             130                 135                 140

Ser Ala Lys Asp Asp Ala Ala Gly Gln Ala Ile Ala Asn Arg Phe Thr
145                 150                 155                 160

Ala Asn Ile Lys Gly Leu Thr Gln Ala Ser Arg Asn Ala Asn Asp Gly
                 165                 170                 175

Ile Ser Ile Ala Gln Thr Thr Glu Gly Ala Leu Asn Glu Ile Asn Asn
             180                 185                 190

Asn Leu Gln Arg Val Arg Glu Leu Ala Val Gln Ser Ala Asn Ser Thr
             195                 200                 205

Asn Ser Gln Ser Asp Leu Asp Ser Ile Gln Ala Glu Ile Thr Gln Arg
             210                 215                 220

Leu Asn Glu Ile Asp Arg Val Ser Gly Gln Thr Gln Phe Asn Gly Val
225                 230                 235                 240

Lys Val Leu Ala Gln Asp Asn Thr Leu Thr Ile Gln Val Gly Ala Asn
                 245                 250                 255

Asp Gly Glu Thr Ile Asp Ile Asp Leu Lys Gln Ile Asn Ser Gln Thr
             260                 265                 270

Leu Gly Leu Asp Ser Leu Asn Val His Gly Ala Pro Val Asp Pro Ala
             275                 280                 285

Ser Pro Trp Thr Glu Asn Pro Leu Gln Lys Ile Asp Ala Ala Leu Ala
             290                 295                 300

Gln Val Asp Ala Leu Arg Ser Asp Leu Gly Ala Val Gln Asn Arg Phe
305                 310                 315                 320

Asn Ser Ala Ile Thr Asn Leu Gly Asn Thr Val Asn Asn Leu Ser Glu
                 325                 330                 335

Ala Arg Ser Arg Ile Glu Asp Ser Asp Tyr Ala Thr Glu Val Ser Asn
             340                 345                 350

Met Ser Arg Ala Gln Ile Leu Gln Gln Ala Gly Thr Ser Val Leu Ala
             355                 360                 365

Gln Ala Asn Gln Val Pro Gln Asn Val Leu Ser Leu Leu Arg
370                 375                 380

<210> SEQ ID NO 22
<211> LENGTH: 368
<212> TYPE: PRT
<213> ORGANISM: Artificial sequence
<220> FEATURE:
<223> OTHER INFORMATION: Synthetic construct
```

<400> SEQUENCE: 22

```
Met Gly His His His His His Ala Ser Gly Ser Trp Glu Trp
1               5                   10                  15

Asn Ala Arg Trp Asp Glu Trp Glu Asn Asp Trp Asn Asp Trp Arg Glu
            20                  25                  30

Asp Trp Gln Ala Trp Arg Asp Asp Trp Ala Arg Trp Arg Ala Thr Trp
        35                  40                  45

Met Gly Gly Arg Leu Leu Ser Arg Leu Glu Arg Leu Glu Arg Arg Asn
50                  55                  60

Glu Glu Leu Arg Arg Leu Leu Gln Leu Leu Arg Asn Arg Leu Glu Arg
65                  70                  75                  80

Leu Ala Gln Phe Val Arg Ala Leu Ser Met Gln Asn Ala Glu Leu Glu
                85                  90                  95

Arg Arg Leu Glu Glu Leu Ala Arg Gly Ser Gly Ser Ser Ala Arg Leu
            100                 105                 110

Ser Asp Leu Glu Ala Asn Asn Ala Val Arg Gly Glu Ser Lys Ile Thr
        115                 120                 125

Val Asn Gly Ala Glu Tyr Thr Ala Asn Ala Thr Gly Asp Arg Ile Thr
130                 135                 140

Leu Ala Gly Arg Thr Met Phe Ile Asp Arg Thr Ala Ser Gly Val Ser
145                 150                 155                 160

Thr Leu Ile Asn Glu Asp Ala Ala Ala Arg Arg Ser Thr Ala Asn
                165                 170                 175

Pro Leu Ala Ser Ile Asp Ser Ala Leu Ser Arg Val Asp Ala Val Arg
            180                 185                 190

Ser Ser Leu Gly Ala Ile Gln Asn Arg Phe Asp Ser Ala Lys Ala Lys
        195                 200                 205

Lys Lys Asp Gly Lys Asp Asp Lys Asp Ser Lys Asn Ala Asn Asp Gly
210                 215                 220

Ile Ser Ile Ala Gln Thr Thr Glu Gly Ala Leu Asn Glu Ile Asn Asn
225                 230                 235                 240

Asn Leu Gln Arg Val Arg Glu Leu Ser Val Gln Ala Thr Asn Gly Thr
                245                 250                 255

Asn Ser Asp Ser Asp Leu Arg Ser Ile Gln Asp Glu Ile Gln Gln Arg
            260                 265                 270

Leu Glu Glu Ile Asp Arg Val Ser Asn Gln Thr Gln Phe Asn Gly Val
        275                 280                 285

Lys Val Leu Ser Gln Asp Asn Gln Met Lys Ile Gln Val Gly Ala Lys
290                 295                 300

Asp Gly Glu Thr Ile Thr Ile Asp Leu Gln Lys Ile Asp Val Lys Ser
305                 310                 315                 320

Leu Gly Leu Asp Gly Phe Asn Val Asn Gly Pro Arg Glu Ala Thr Val
                325                 330                 335

Gly Asp Leu Arg Ser Ser Phe Arg Asn Val Thr Gly Tyr Asp Thr Tyr
            340                 345                 350

Ala Ala Gly Ala Asp Arg Tyr Arg Val Asp Ile Asn Ser Gly Ala Val
        355                 360                 365
```

<210> SEQ ID NO 23
<211> LENGTH: 277
<212> TYPE: PRT
<213> ORGANISM: Artificial sequence
<220> FEATURE:
<223> OTHER INFORMATION: Synthetic construct

<400> SEQUENCE: 23

```
Met Ala Gln Val Ile Asn Thr Asn Ser Leu Ser Leu Leu Thr Gln Asn
1               5                   10                  15

Asn Leu Asn Lys Ser Gln Ser Ala Leu Gly Thr Ala Ile Glu Arg Leu
            20                  25                  30

Ser Ser Gly Leu Arg Ile Asn Ser Ala Lys Asp Asp Ala Ala Gly Gln
        35                  40                  45

Ala Ile Ala Asn Arg Phe Thr Ala Asn Ile Lys Gly Leu Thr Gln Ala
    50                  55                  60

Ser Arg Asn Ala Asn Asp Gly Ile Ser Ile Ala Gln Thr Thr Glu Gly
65                  70                  75                  80

Ala Leu Asn Glu Ile Asn Asn Asn Leu Gln Arg Val Arg Glu Leu Ala
                85                  90                  95

Val Gln Ser Ala Asn Ser Thr Asn Ser Gln Ser Asp Leu Asp Ser Ile
            100                 105                 110

Gln Ala Glu Ile Thr Gln Arg Leu Asn Glu Ile Asp Arg Val Ser Gly
        115                 120                 125

Gln Thr Gln Phe Asn Gly Val Lys Val Leu Ala Gln Asp Asn Thr Leu
    130                 135                 140

Thr Ile Gln Val Gly Ala Asn Asp Gly Glu Thr Ile Asp Ile Asp Leu
145                 150                 155                 160

Lys Gln Ile Asn Ser Gln Thr Leu Gly Leu Asp Ser Leu Asn Val His
                165                 170                 175

Gly Ala Pro Val Asp Pro Ala Ser Pro Trp Thr Glu Asn Pro Leu Gln
            180                 185                 190

Lys Ile Asp Ala Ala Leu Ala Gln Val Asp Ala Leu Arg Ser Asp Leu
        195                 200                 205

Gly Ala Val Gln Asn Arg Phe Asn Ser Ala Ile Thr Asn Leu Gly Asn
    210                 215                 220

Thr Val Asn Asn Leu Ser Glu Ala Arg Ser Arg Ile Glu Asp Ser Asp
225                 230                 235                 240

Tyr Ala Thr Glu Val Ser Asn Met Ser Arg Ala Gln Ile Leu Gln Gln
                245                 250                 255

Ala Gly Thr Ser Val Leu Ala Gln Ala Asn Gln Val Pro Gln Asn Val
            260                 265                 270

Leu Ser Leu Leu Arg
        275
```

<210> SEQ ID NO 24
<211> LENGTH: 260
<212> TYPE: PRT
<213> ORGANISM: Artificial sequence
<220> FEATURE:
<223> OTHER INFORMATION: Synthetic construct

<400> SEQUENCE: 24

```
Ser Ala Arg Leu Ser Asp Leu Glu Ala Asn Asn Ala Val Arg Gly Glu
1               5                   10                  15

Ser Lys Ile Thr Val Asn Gly Ala Glu Tyr Thr Ala Asn Ala Thr Gly
            20                  25                  30

Asp Arg Ile Thr Leu Ala Gly Arg Thr Met Phe Ile Asp Arg Thr Ala
        35                  40                  45

Ser Gly Val Ser Thr Leu Ile Asn Glu Asp Ala Ala Ala Arg Arg
    50                  55                  60
```

```
Ser Thr Ala Asn Pro Leu Ala Ser Ile Asp Ser Ala Leu Ser Arg Val
 65                  70                  75                  80

Asp Ala Val Arg Ser Ser Leu Gly Ala Ile Gln Asn Arg Phe Asp Ser
                 85                  90                  95

Ala Lys Ala Lys Lys Asp Gly Lys Asp Asp Lys Asp Ser Lys Asn
            100                 105                 110

Ala Asn Asp Gly Ile Ser Ile Ala Gln Thr Thr Glu Gly Ala Leu Asn
            115                 120                 125

Glu Ile Asn Asn Asn Leu Gln Arg Val Arg Glu Leu Ser Val Gln Ala
        130                 135                 140

Thr Asn Gly Thr Asn Ser Asp Ser Asp Leu Arg Ser Ile Gln Asp Glu
145                 150                 155                 160

Ile Gln Gln Arg Leu Glu Glu Ile Asp Arg Val Ser Asn Gln Thr Gln
                165                 170                 175

Phe Asn Gly Val Lys Val Leu Ser Gln Asp Asn Gln Met Lys Ile Gln
            180                 185                 190

Val Gly Ala Lys Asp Gly Glu Thr Ile Thr Ile Asp Leu Gln Lys Ile
        195                 200                 205

Asp Val Lys Ser Leu Gly Leu Asp Gly Phe Asn Val Asn Gly Pro Arg
    210                 215                 220

Glu Ala Thr Val Gly Asp Leu Arg Ser Ser Phe Arg Asn Val Thr Gly
225                 230                 235                 240

Tyr Asp Thr Tyr Ala Ala Gly Ala Asp Arg Tyr Arg Val Asp Ile Asn
                245                 250                 255

Ser Gly Ala Val
            260

<210> SEQ ID NO 25
<211> LENGTH: 12
<212> TYPE: PRT
<213> ORGANISM: Artificial sequence
<220> FEATURE:
<223> OTHER INFORMATION: Synthetic construct

<400> SEQUENCE: 25

Lys Ala Lys Lys Lys Asp Gly Lys Asp Asp Lys Asp
1               5                   10

<210> SEQ ID NO 26
<211> LENGTH: 390
<212> TYPE: PRT
<213> ORGANISM: Artificial sequence
<220> FEATURE:
<223> OTHER INFORMATION: Synthetic construct

<400> SEQUENCE: 26

Met Gly Asp Lys His His His His His His Lys Asp Gly Ser Asp Lys
1               5                   10                  15

Gly Ser Trp Glu Glu Trp Asn Ala Arg Trp Asp Glu Trp Glu Asn Asp
            20                  25                  30

Trp Asn Asp Trp Arg Glu Asp Trp Gln Ala Trp Arg Asp Asp Trp Ala
        35                  40                  45

Arg Trp Arg Ala Thr Trp Met Gly Gly Arg Leu Leu Ser Arg Leu Glu
    50                  55                  60

Arg Leu Glu Arg Arg Asn Glu Glu Leu Arg Arg Leu Gln Leu Leu
65                  70                  75                  80

Arg Asn Arg Leu Glu Arg Leu Ala Gln Phe Val Arg Ala Leu Ser Met
                85                  90                  95
```

Gln Asn Ala Glu Leu Glu Arg Arg Leu Glu Leu Ala Arg Gly Met
                100                 105                 110

Ala Gln Val Ile Asn Thr Asn Ser Leu Ser Leu Thr Gln Asn Asn
            115                 120                 125

Leu Asn Arg Ser Gln Ser Ala Leu Gly Thr Ala Ile Glu Arg Leu Ser
        130                 135                 140

Ser Gly Leu Arg Ile Asn Ser Ala Arg Asp Asp Ala Ala Gly Gln Ala
145                 150                 155                 160

Ile Ala Asn Arg Phe Thr Ala Asn Ile Arg Gly Leu Thr Gln Ala Ser
                165                 170                 175

Arg Asn Ala Asn Asp Gly Ile Ser Ile Ala Gln Thr Thr Glu Gly Ala
            180                 185                 190

Leu Asn Glu Ile Asn Asn Asn Leu Gln Arg Val Arg Glu Leu Ala Val
        195                 200                 205

Gln Ser Ala Asn Ser Thr Asn Ser Gln Ser Asp Leu Asp Ser Ile Gln
210                 215                 220

Ala Glu Ile Thr Gln Arg Leu Asn Glu Ile Asp Arg Val Ser Gly Gln
225                 230                 235                 240

Thr Gln Phe Asn Gly Val Arg Val Leu Ala Gln Asp Asn Thr Leu Thr
                245                 250                 255

Ile Gln Val Gly Ala Asn Asp Gly Glu Thr Ile Asp Ile Asp Leu Arg
            260                 265                 270

Gln Ile Asn Ser Gln Thr Leu Gly Leu Asp Gln Leu Asn Val Gln Gln
        275                 280                 285

Lys Tyr Lys Asp Gly Asp Lys Gly Asp Asp Lys Thr Glu Asn Pro Leu
290                 295                 300

Gln Arg Ile Asp Ala Ala Leu Ala Gln Val Asp Ala Leu Arg Ser Asp
305                 310                 315                 320

Leu Gly Ala Val Gln Asn Arg Phe Asn Ser Ala Ile Thr Asn Leu Gly
                325                 330                 335

Asn Thr Val Asn Asn Leu Ser Glu Ala Arg Ser Arg Ile Glu Asp Ser
            340                 345                 350

Asp Tyr Ala Thr Glu Val Ser Asn Met Ser Arg Ala Gln Ile Leu Gln
        355                 360                 365

Gln Ala Gly Thr Ser Val Leu Ala Gln Ala Asn Gln Val Pro Gln Asn
370                 375                 380

Val Leu Ser Leu Leu Arg
385                 390

<210> SEQ ID NO 27
<211> LENGTH: 28
<212> TYPE: PRT
<213> ORGANISM: Artificial sequence
<220> FEATURE:
<223> OTHER INFORMATION: Synthetic construct

<400> SEQUENCE: 27

Glu Leu Arg Arg Leu Leu Gln Leu Leu Arg Asn Arg Leu Glu Arg Leu
1               5                   10                  15

Ala Gln Phe Val Arg Ala Leu Ser Met Gln Asn Ala
            20                  25

<210> SEQ ID NO 28
<211> LENGTH: 279
<212> TYPE: PRT
<213> ORGANISM: Artificial sequence

```
<220> FEATURE:
<223> OTHER INFORMATION: Synthetic construct

<400> SEQUENCE: 28

Met Ala Gln Val Ile Asn Thr Asn Ser Leu Ser Leu Leu Thr Gln Asn
1               5                   10                  15

Asn Leu Asn Arg Ser Gln Ser Ala Leu Gly Thr Ala Ile Glu Arg Leu
            20                  25                  30

Ser Ser Gly Leu Arg Ile Asn Ser Ala Arg Asp Asp Ala Ala Gly Gln
        35                  40                  45

Ala Ile Ala Asn Arg Phe Thr Ala Asn Ile Arg Gly Leu Thr Gln Ala
    50                  55                  60

Ser Arg Asn Ala Asn Asp Gly Ile Ser Ile Ala Gln Thr Thr Glu Gly
65                  70                  75                  80

Ala Leu Asn Glu Ile Asn Asn Leu Gln Arg Val Arg Glu Leu Ala
                85                  90                  95

Val Gln Ser Ala Asn Ser Thr Asn Ser Gln Ser Asp Leu Asp Ser Ile
            100                 105                 110

Gln Ala Glu Ile Thr Gln Arg Leu Asn Glu Ile Asp Arg Val Ser Gly
        115                 120                 125

Gln Thr Gln Phe Asn Gly Val Arg Val Leu Ala Gln Asp Asn Thr Leu
    130                 135                 140

Thr Ile Gln Val Gly Ala Asn Asp Gly Glu Thr Ile Asp Ile Asp Leu
145                 150                 155                 160

Arg Gln Ile Asn Ser Gln Thr Leu Gly Leu Asp Gln Leu Asn Val Gln
                165                 170                 175

Gln Lys Tyr Lys Asp Gly Asp Lys Gly Asp Asp Lys Thr Glu Asn Pro
            180                 185                 190

Leu Gln Arg Ile Asp Ala Ala Leu Ala Gln Val Asp Ala Leu Arg Ser
        195                 200                 205

Asp Leu Gly Ala Val Gln Asn Arg Phe Asn Ser Ala Ile Thr Asn Leu
    210                 215                 220

Gly Asn Thr Val Asn Asn Leu Ser Glu Ala Arg Ser Arg Ile Glu Asp
225                 230                 235                 240

Ser Asp Tyr Ala Thr Glu Val Ser Asn Met Ser Arg Ala Gln Ile Leu
                245                 250                 255

Gln Gln Ala Gly Thr Ser Val Leu Ala Gln Ala Asn Gln Val Pro Gln
            260                 265                 270

Asn Val Leu Ser Leu Leu Arg
        275

<210> SEQ ID NO 29
<211> LENGTH: 13
<212> TYPE: PRT
<213> ORGANISM: Artificial sequence
<220> FEATURE:
<223> OTHER INFORMATION: Synthetic construct

<400> SEQUENCE: 29

Lys Ala Lys Lys Lys Asp Gly Lys Asp Asp Lys Asp Ser
1               5                   10

<210> SEQ ID NO 30
<211> LENGTH: 260
<212> TYPE: PRT
<213> ORGANISM: Artificial sequence
<220> FEATURE:
<223> OTHER INFORMATION: Synthetic construct
```

<400> SEQUENCE: 30

Ser Ala Arg Leu Ser Asp Leu Glu Ala Asn Asn Ala Val Arg Gly Glu
1               5                   10                  15

Ser Lys Ile Thr Val Asn Gly Ala Glu Tyr Thr Ala Asn Ala Thr Gly
            20                  25                  30

Asp Arg Ile Thr Leu Ala Gly Arg Thr Met Phe Ile Asp Arg Thr Ala
        35                  40                  45

Ser Gly Val Ser Thr Leu Ile Asn Glu Asp Ala Ala Ala Arg Arg
    50                  55                  60

Ser Thr Ala Asn Pro Leu Ala Ser Ile Asp Ser Ala Leu Ser Arg Val
65                  70                  75                  80

Asp Ala Val Arg Ser Ser Leu Gly Ala Ile Gln Asn Arg Phe Asp Ser
                85                  90                  95

Ala Lys Ala Lys Lys Asp Gly Lys Asp Lys Asp Ser Lys Asn
            100                 105                 110

Ala Asn Asp Gly Ile Ser Ile Ala Gln Thr Thr Glu Gly Ala Leu Asn
            115                 120                 125

Glu Ile Asn Asn Asn Leu Gln Arg Val Arg Glu Leu Ser Val Gln Ala
            130                 135                 140

Thr Asn Gly Thr Asn Ser Asp Ser Asp Leu Arg Ser Ile Gln Asp Glu
145                 150                 155                 160

Ile Gln Gln Arg Leu Glu Glu Ile Asp Arg Val Ser Asn Gln Thr Gln
                165                 170                 175

Phe Asn Gly Val Lys Val Leu Ser Gln Asp Asn Gln Met Lys Ile Gln
            180                 185                 190

Val Gly Ala Lys Asp Gly Glu Thr Ile Thr Ile Asp Leu Gln Lys Ile
            195                 200                 205

Asp Val Lys Ser Leu Gly Leu Asp Gly Phe Asn Val Asn Gly Pro Arg
        210                 215                 220

Glu Ala Thr Val Gly Asp Leu Arg Ser Ser Phe Arg Asn Val Thr Gly
225                 230                 235                 240

Tyr Asp Thr Tyr Ala Ala Gly Ala Asp Arg Tyr Arg Val Asp Ile Asn
                245                 250                 255

Ser Gly Ala Val
            260

<210> SEQ ID NO 31
<211> LENGTH: 8
<212> TYPE: PRT
<213> ORGANISM: Artificial sequence
<220> FEATURE:
<223> OTHER INFORMATION: Synthetic construct

<400> SEQUENCE: 31

Gly Lys Asp Gly Lys Asp Gly Ser
1               5

<210> SEQ ID NO 32
<211> LENGTH: 14
<212> TYPE: PRT

```
<213> ORGANISM: Artificial sequence
<220> FEATURE:
<223> OTHER INFORMATION: Synthetic construct

<400> SEQUENCE: 32

Gly Lys Asp Gly Lys Asp Gly Lys Asp Gly Lys Asp Gly Ser
1               5                   10
```

FLAGELLIN-CONTAINING PROTEIN NANOPARTICLES AS A VACCINE PLATFORM

FIELD OF THE INVENTION

The present invention relates to self-assembling protein nanoparticles incorporating the protein sequence of the TLR5 binding protein flagellin as an in-built adjuvant. Furthermore, the invention relates to the use of such nanoparticles for vaccination.

BACKGROUND OF THE INVENTION

The first line of defense against invading pathogens is via the host's innate immunity, and the Toll-like receptors (TLRs), which are membrane bound receptors, play a key role in it (Yoon S. I. et al., Science 2012, 335:859-64). TLRs recognize antigens with a highly conserved molecular structure using their leucine-rich repeat (LRR) ectodomains. This LRR has a shape of a horseshoe. Each TLR has a distinct ligand-binding domain that recognizes its particular molecular antigen, which can be special forms of viral or bacterial nucleic acids, bacterial surface molecules such as lipopolysaccharides (LPS) or other pathogen associated molecules with a particular pattern. Even though they recognize a variety of unrelated molecular antigens, all known agonist-activated TLR structures, i.e. TLRs that have recognized and bound their molecular antigen, form a similar dimer organization upon antigen binding, which brings their C-terminal regions close to each other, which in turn activates their intracellular Toll/Interleukin-1 Receptor (TIR) domains and thus initiates the cellular signaling cascades.

With respect to the scope of this invention it is interesting to note that of the many different TLR receptors TLR5 is the only protein-binding TLR that is conserved in vertebrates from fish to mammals. TLR5 binds a disassembled form of whip-like flagellar filament flagellin from β- and γ-proteobacteria, which is responsible for locomotion flagellin. Recent crystallographic studies have shown a dimeric complex between flagellin and TLR5. Upon binding of flagellin to TLR5 the MyD88-dependent signaling pathway is induced which in turn activates the proinflammatory transcription factor NF-kB in dendritic cells, monocytes, and epithelial cells, ultimately leading to innate immune responses against flagellated bacteria.

Flagellin has a molecular architecture that is composed of four domains D0, D1, D2 and D3. The protein chain starts with the N-terminus in the D0 domain and runs in a big loop through the other domains D1, D2 and D3 to the tip of the molecule where it turns and runs back through D3, D2 and D1 to bring its C-terminal end in the D0 domain very close to the N-terminal end. Flagellin has two modes of activation of the innate immune system. The first mode is by binding to the TLR5 receptor mainly through a highly conserved portion of its D1 domain (Yoon et al., loc. cit.). The other mode of activation is by interaction with the inflammasome mainly through a highly conserved C-terminal portion of its D0 domain (Lightfield K. L. et al., Nat Immunol. 2008, 9:1171-8).

Flagellin has been used as a conventional adjuvant, i.e. as a separate entity that is injected together with the antigen, or it has also been engineered to contain the antigen itself within its own molecular architecture. The second approach has the advantage that the adjuvant effect is co-localized with the effect of the antigen, hence the dosage of the adjuvant can be significantly reduced and as a consequence the side effects can also significantly be reduced.

One of the possible limitations of flagellin is its potential to induce inflammatory immune responses. It might be possible to reduce the inflammatory part of the immune stimulation by engineering flagellin constructs that lack the C-terminal portion of D0 that interact with the inflammasome.

Many adjuvants have significant limitations in their use due to their severe side effects. For example Freund's complete adjuvant, which is a very strong immunostimulatory formulation, may not even be used in animal experiments anymore. Currently, there are only very few approved adjuvants for human use, the most important being alumn. One possible way to limit the side effects of systemically applied adjuvants is their formulation as a particulate system, i.e. incorporating adjuvants into a particulate form or into an oily emulsion that may limit the side effects and concentrate the adjuvant close to the antigen of interest. Thus, the antigen and the adjuvant may reach the same lymph node at the same time, hence increasing the adjuvant effect while lowering the systemic side effects of the adjuvant.

Flagellin is a particularly interesting adjuvant for use in protein nanoparticles such as those described in WO 2004/071493, since flagellin is a protein itself, as opposed to many other adjuvants that are small molecules, such as imiquimod, or nucleic acid based entities, such as CpG. Since flagellin is a protein, it can be engineered onto the nanoparticle by means of molecular biology without the need of chemical cross-linking.

SUMMARY OF THE INVENTION

The invention relates to a self-assembling protein nanoparticle consisting of aggregates of a multitude of building blocks of formula (Ia) or (Ib)

$$X\text{-}ND1\text{-}L1\text{-}ND2\text{-}FLA \qquad (Ia)$$

or $$FLA\text{-}ND1\text{-}L1\text{-}ND2\text{-}X \qquad (Ib),$$

consisting of a continuous chain comprising a protein oligomerization domain ND1, a linker L1, a protein oligomerization domain ND2, a derivative of flagellin FLA, and a further substituent X, wherein ND1 is a protein that forms oligomers $(ND1)_m$ of m subunits ND1, ND2 is a protein that forms oligomers $(ND2)_n$ of n subunits ND2, m and n each is a figure between 2 and 10, with the proviso that m is not equal n and not a multiple of n, and n is not a multiple of m, L1 is a bond or a short flexible linker, FLA is flagellin, or a derivative of flagellin lacking parts of the flagellin amino acid sequence but at least containing the TLR5 binding domain D1, and wherein optionally the missing domain(s) are replaced by a flexible linker segment of 1 to 20 amino acids joining the two ends of the remaining flagellin sequence, or are replaced by a fully folded protein antigen;

X is absent or a peptide or protein sequence comprising 1 to 1000 amino acids, optionally co-assembled with a multitude of building blocks of the formula (II)

$$Y\text{-}ND3\text{-}L2\text{-}ND4\text{-}Z \qquad (II),$$

consisting of a continuous chain comprising a protein oligomerization domain ND3, a linker L2, a protein oligomerization domain ND4, and further substituents Y and Z, wherein ND3 is a protein that forms oligomers $(ND3)_y$ of y subunits ND3, ND4 is a protein that forms oligomers $(ND4)_z$ of z subunits ND4, y and z each is a figure between 2 and 10, with the proviso that y is not equal z and not a multiple of z, and z is not a multiple of y, and wherein either ND3 is identical to ND1, or ND4 is identical to ND2 or both ND3 and ND4 are identical to ND1 and ND2, respectively, L2 is a bond or a short flexible linker that may be different from L1 or identical to L1, and Y and Z are, independently of each other, absent or a peptide or protein sequence comprising 1 to 1000 amino acids.

In the upper left corner the monomer of the flagellin-containing protein chain fused to the oligomerization domains ND2 and ND1 is shown; to the right the nanoparticle co-assembled with ND3-L2-ND4-Z at a ratio of 1:59 assuming T=1 icosahedral symmetry. For clarity the most likely disordered His-tags (X and Y) are not shown.

Figure 1A:
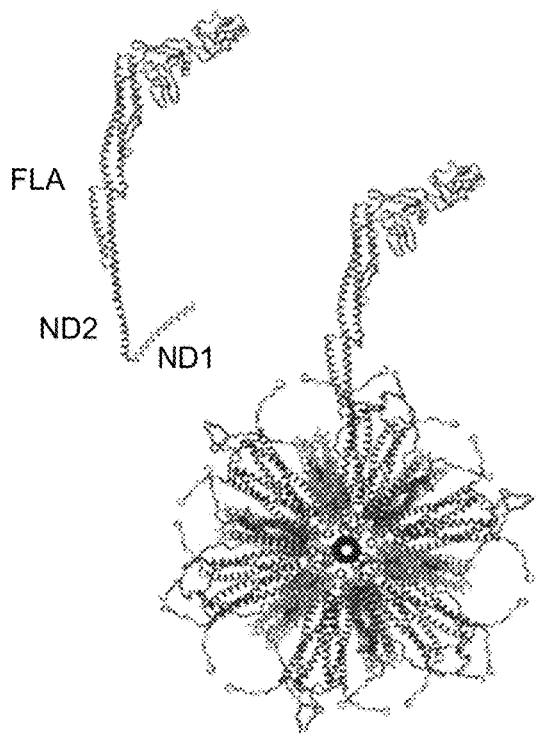
FIGS. 1(A)-1(E): Schematic presentation of different protein nanoparticles composed of a co-assembly of epitope-containing chains and flagellin- or flagellin derivative-containing chains in upright position.

"ND1" and "ND3": pentameric oligomerization domains; "ND2" and "ND4": trimeric oligomerization domains; "FLA": flagellin or flagellin derivative; "Z": epitope FIG. 1(A) A model of flagellin D0-D1-D2-D3 and the corresponding epitope-presenting nanoparticle.

Figure 1B:
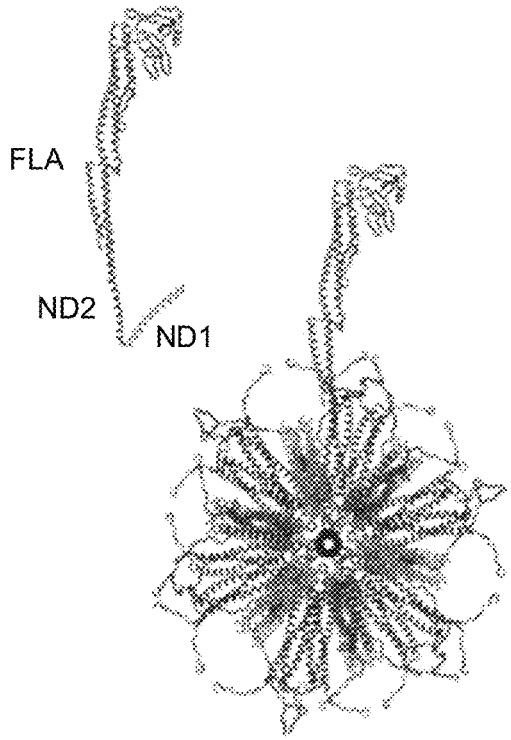

FIG. 1(B) A model of flagellin D0-D1-D2 and the corresponding epitope-presenting nanoparticle.

Figure 1C:
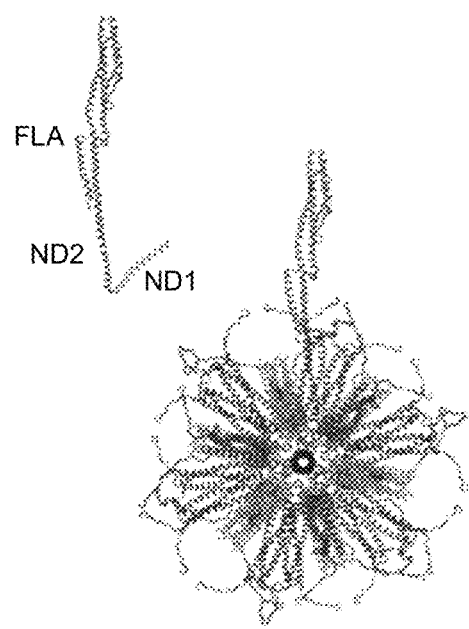

FIG. 1(C) A model of flagellin D0-D1 and the corresponding epitope-presenting nanoparticle.

Figure 1D:
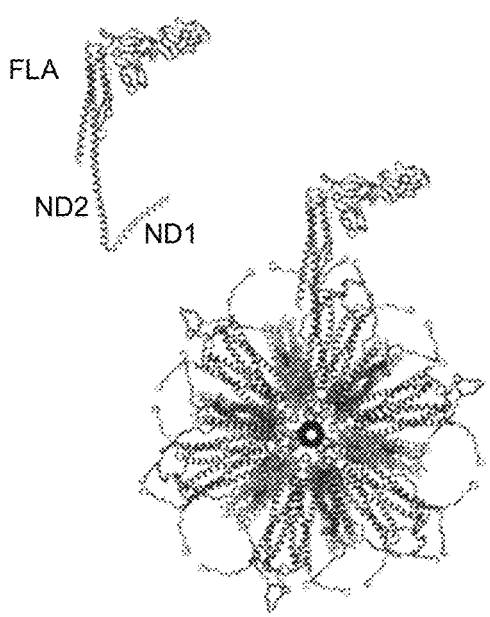

FIG. 1(D) A model of flagellin D1-D2-D3 and the corresponding epitope-presenting nanoparticle.

Figure 1E:

FIG. 1(E) A model of the NANP B-cell epitope (Z) fused to the oligomerization domain ND4 of the ND3-L2-ND4 core.

Figure 2A:
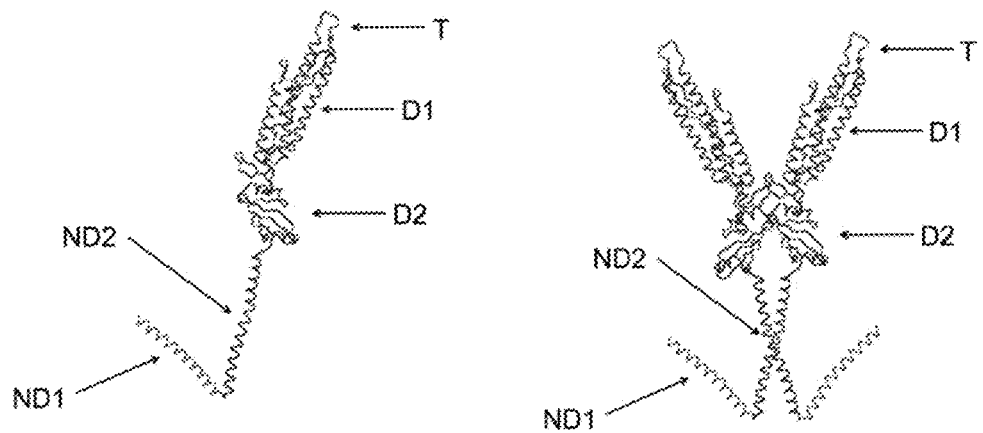
Figure 2B:
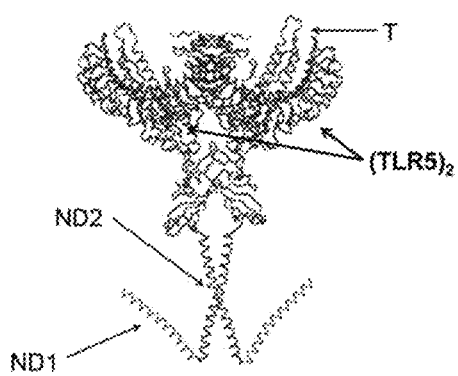

FIGS. 2(A)-2(B): Schematic representation of the interaction of flagellin with TLR5.

Ideally, flagellin has to be dimeric and displayed in a flipped orientation on the nanoparticles. The displayed part of the protein chains starts with the (e.g. pentameric) oligomerization domain ND1 that is joined to the (e.g. dimeric) oligomerization domain ND2 by the linker L, further connected to the flagellin derivative FLA consisting of D2 and then D1 domains of flagellin up to the Tip (T). In the Tip the D1 sequence is joined and folds back onto itself and into the D2 domain. For clarity the most likely disordered His-tags are not shown.

FIG. 2(A) Left: A model of the monomer. Right: A model of the dimer in which flagellin is hold in the right dimeric conformation for the interaction with TLR5.

FIG. 2(B) Upper panel: A model of the flagellin dimer interacting with a TLR5 dimer. Lower panel, left: A model of a fully assembled "flagellin-only" particle in a clipped view. Right: A model of a fully assembled "flagellin-only" particle in a full view.

Figure 3:
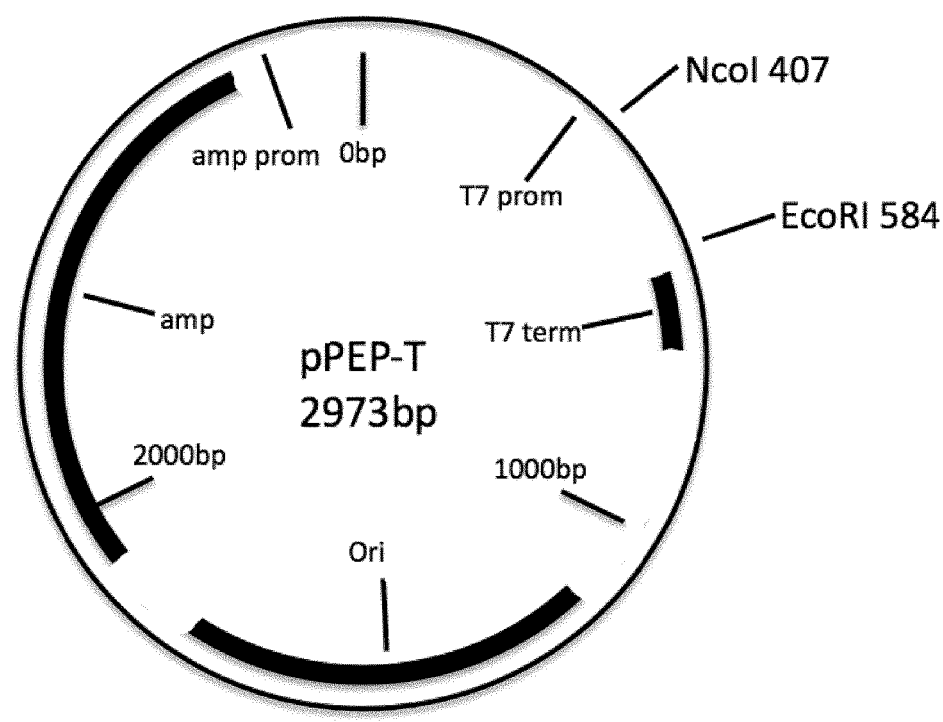

FIG. 3: Vector map of pPEP-T.

"prom": promoter; "term": terminator; "on": origin; "bp": base pairs; "amp": ampicillin resistance gene.

FIGS. 4(A)-4(D): Transmission electron micrographs of protein nanoparticles.

After refolding and co-assembly of recombinantly expressed proteins, samples were adsorbed on carbon-coated grids and negatively stained with 2% uranyl acetate.

Figure 4A:
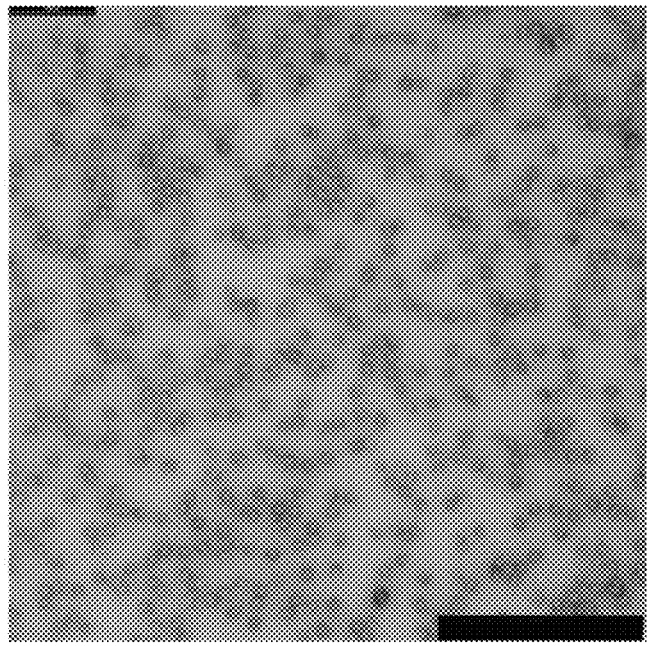

FIG. 4(A) T81c-WRW-8RRVRA-D0-D1: T81c-WRW-8RRVRA-T1BT* co-assembly ratio 12:48 described in section "Design of a FLA-SAPN" and Example 6. The bar represents 500 nm.

Figure 4B:
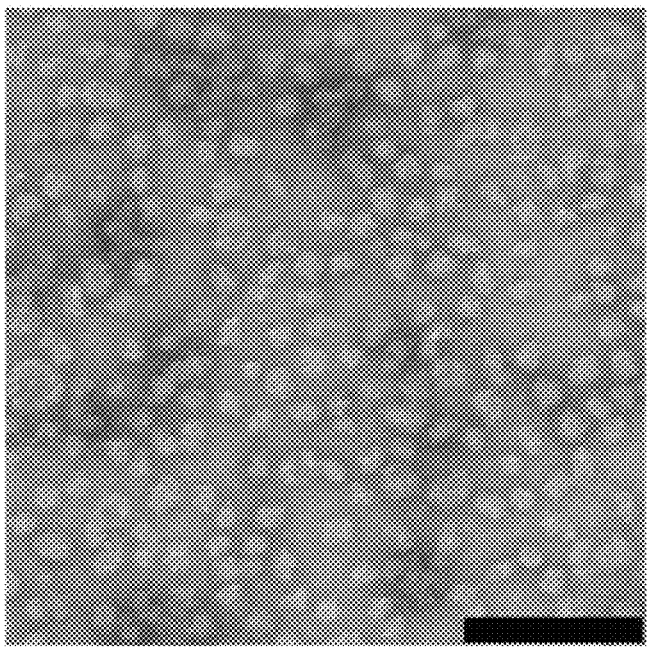

FIG. 4(B) T81c-8-D0-D1: T81c-8-Pf co-assembly ratio 3:57 described in Example 8. The bar represents 200 nm.

Figure 4C:
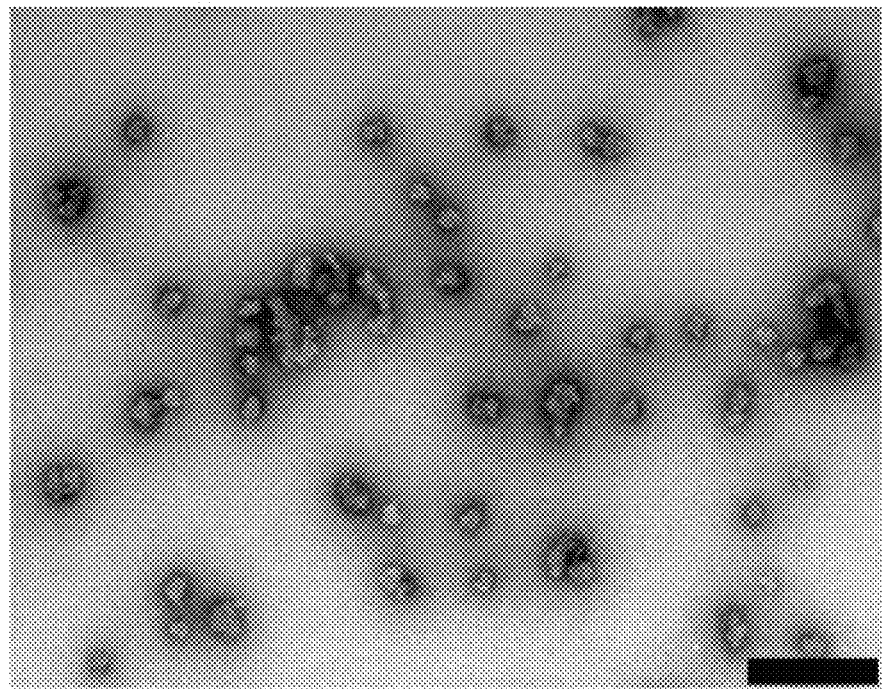

FIG. 4(C) PD52-2i88-PANDORA-D2-D1-ori: PD52-2i88-PANDORA-Noro co-assembly ratio 5:55 described in Example 7. The bar represents 200 nm.

Figure 4D:
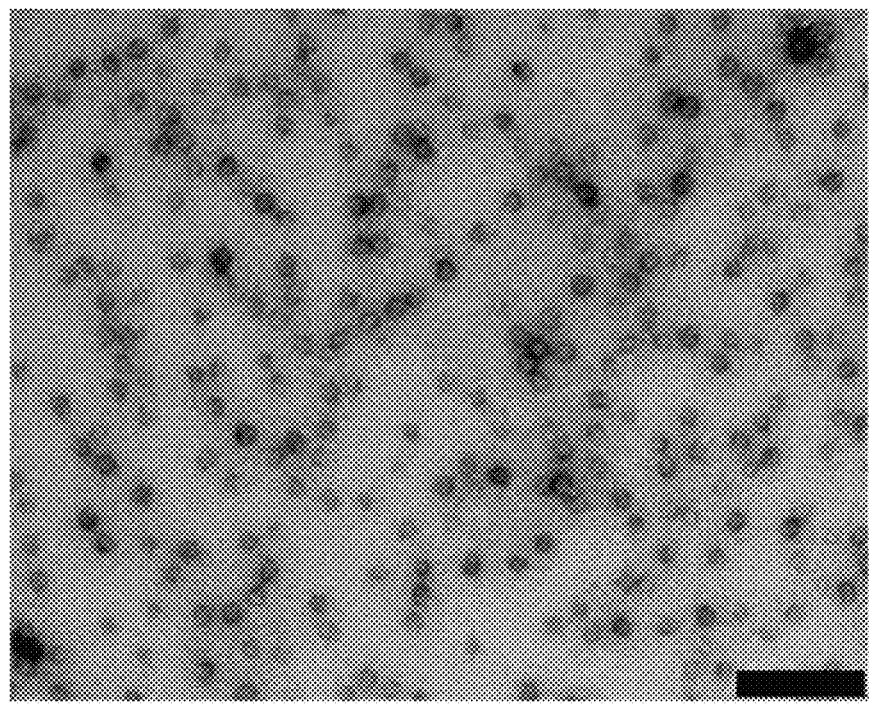

FIG. 4(D) DIM-D0-D1: DIM-D2-D1-tip3_NIC-pept co-assembly ratio 5:55 described in Example 9. The bar represents 200 nm.

Figure 5:
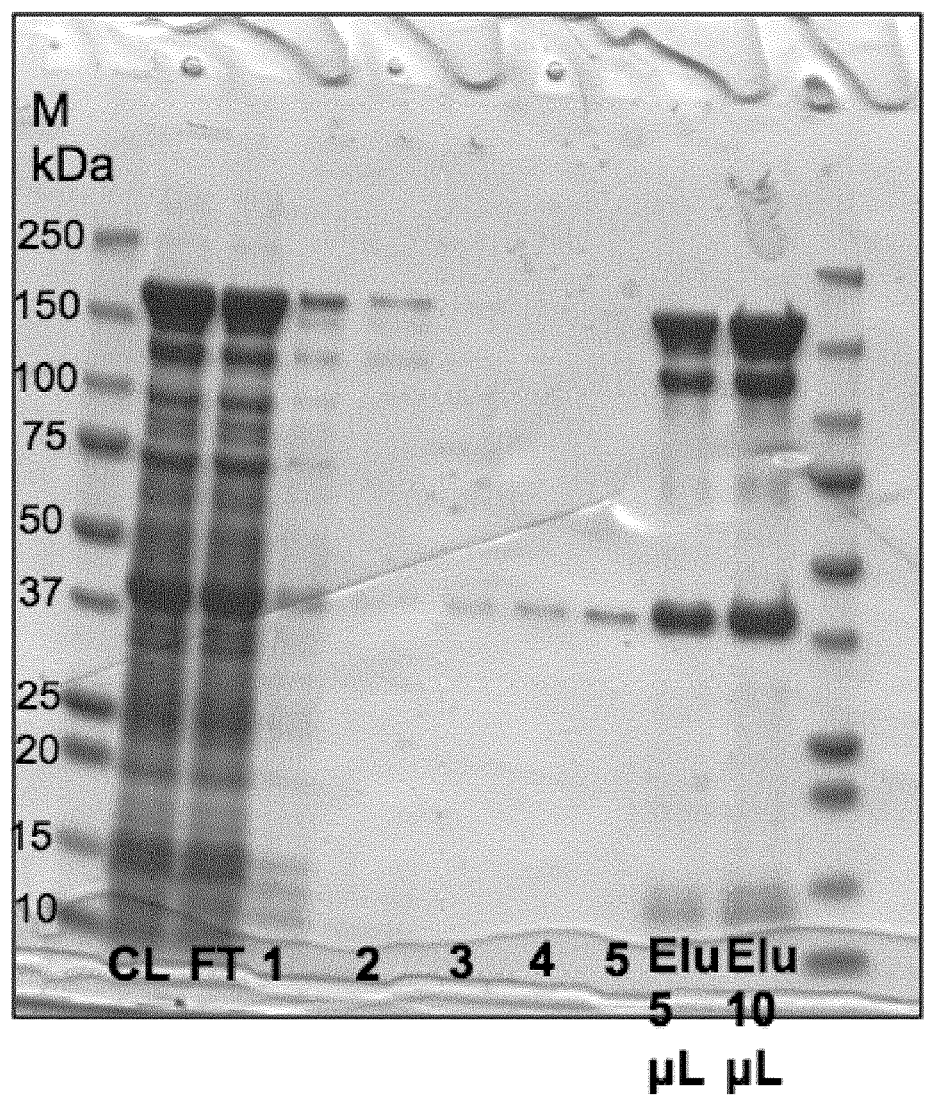

FIG. 5: SDS-PAGE of the construct LONG-D2-D1-ori of Examples 1 and 5.

This construct has a theoretical molecular weight of 41.1 kDa

CL—Cleared lysate
FT—Flow through
1—pH 8.0 wash with 10 mM imidazole
2—pH 8.0 wash with 500 mM $NaH_2PO_4$
3—pH 6.3 wash
4—pH 5.9 wash
5—pH 4.5 wash
Elu—250 mM imidazole elution with 5 and 10 µl of sample applied to the gel.

Figure 6:
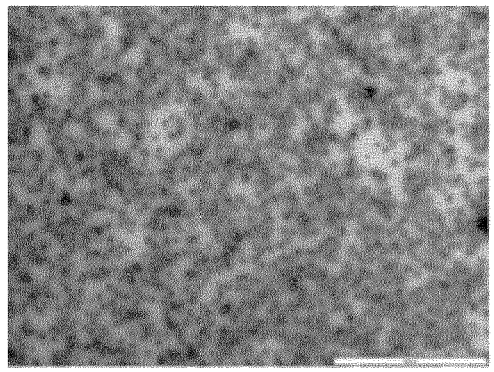
Figure 6:
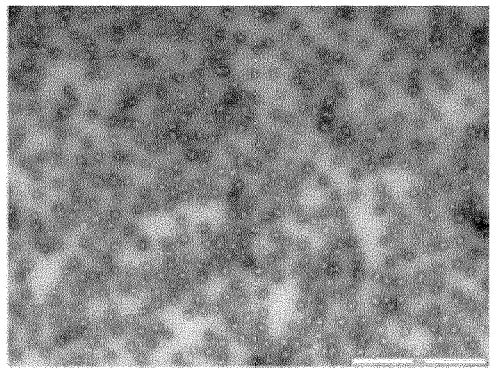
Figure 6:
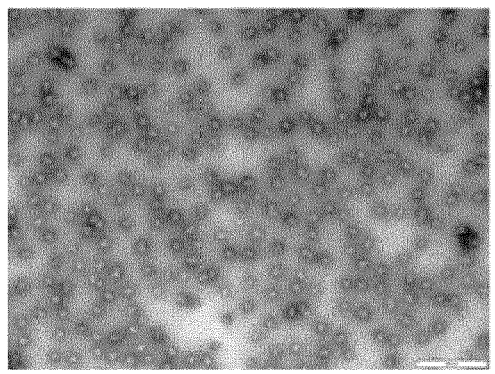
Figure 6:
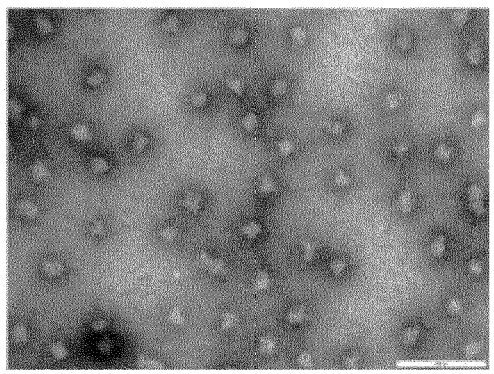

FIG. 6: Transmission electron micrographs of protein nanoparticles of the construct LONG-D2-D1-ori at different resolutions.

After refolding and co-assembly of recombinantly expressed protein, the nanoparticle was adsorbed on carbon-coated grids and negatively stained with 2% uranyl acetate.

The bar represents 1000 nm, 500 nm, 200 nm and 100 nm for the pictures top right, top left, bottom right and bottom left, respectively.

Figure 7A:
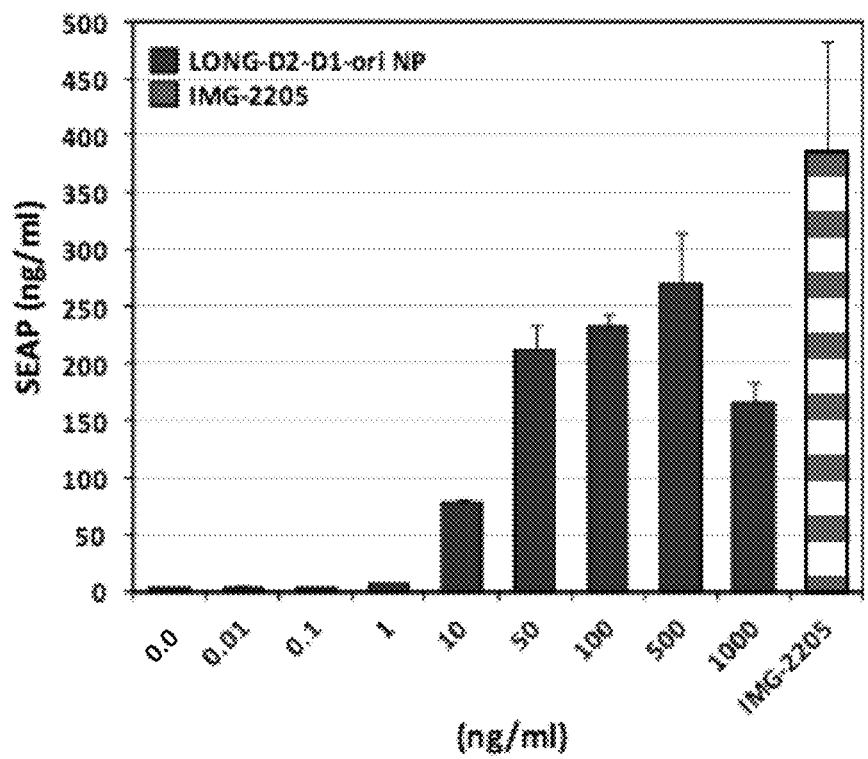
Figure 7A:
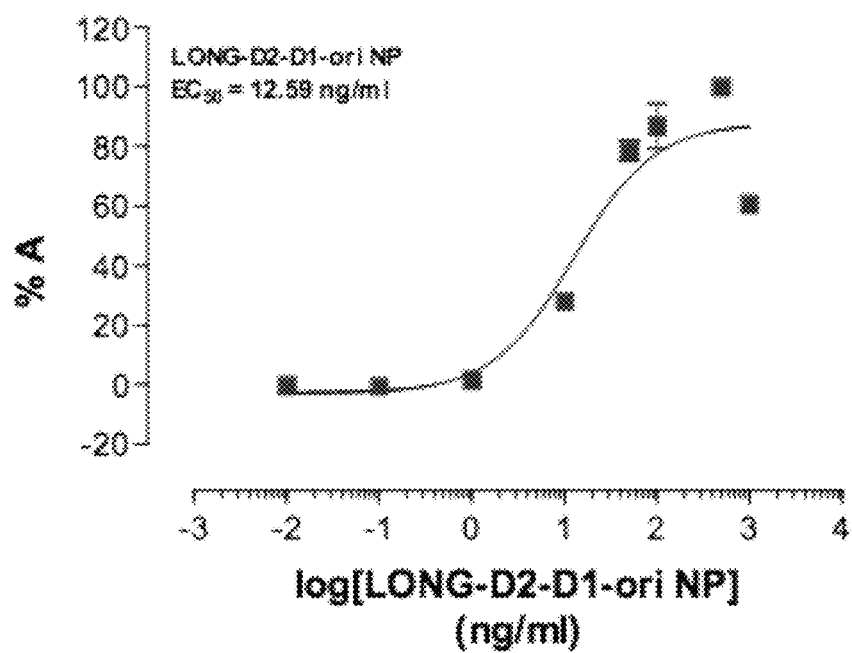
Figure 7B:
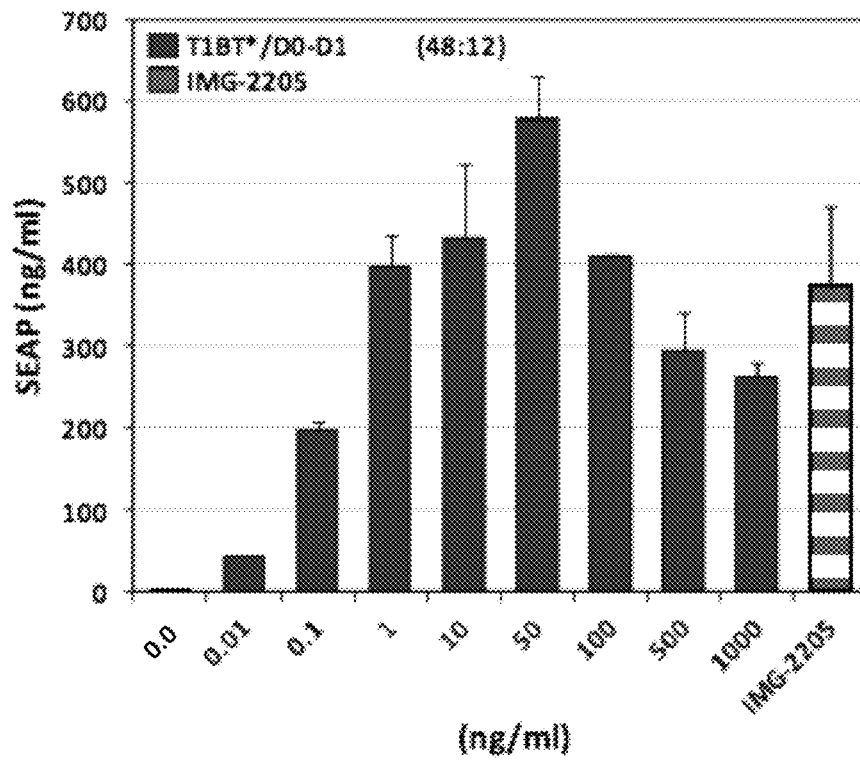
Figure 7B:
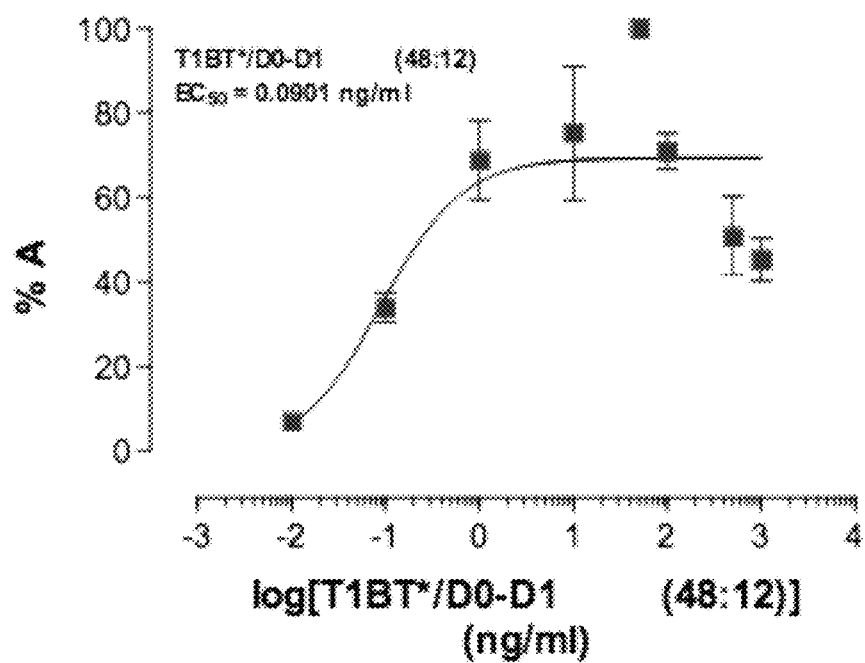
Figure 7C:
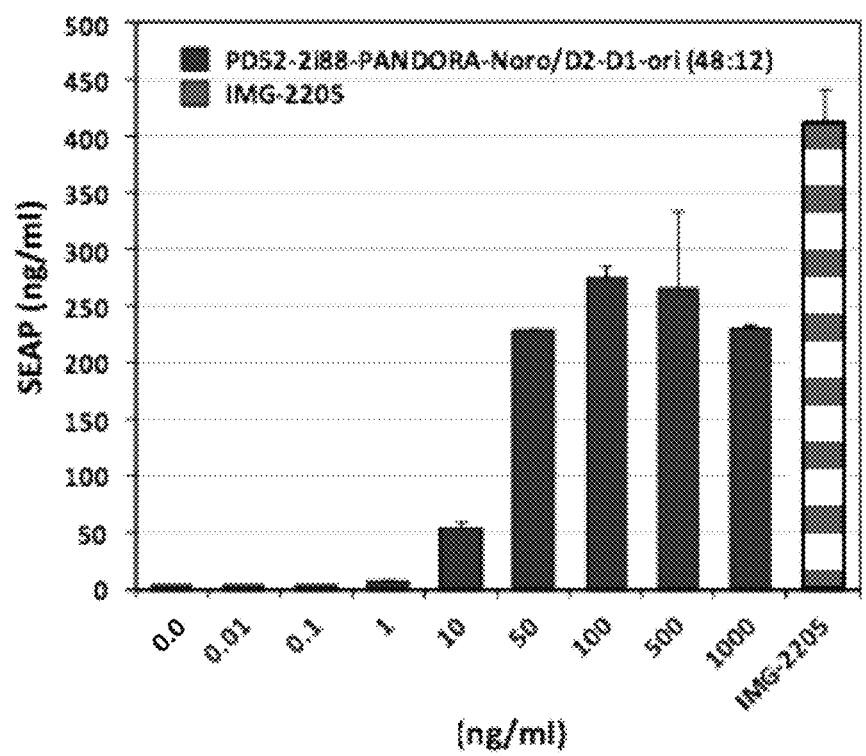
Figure 7C:
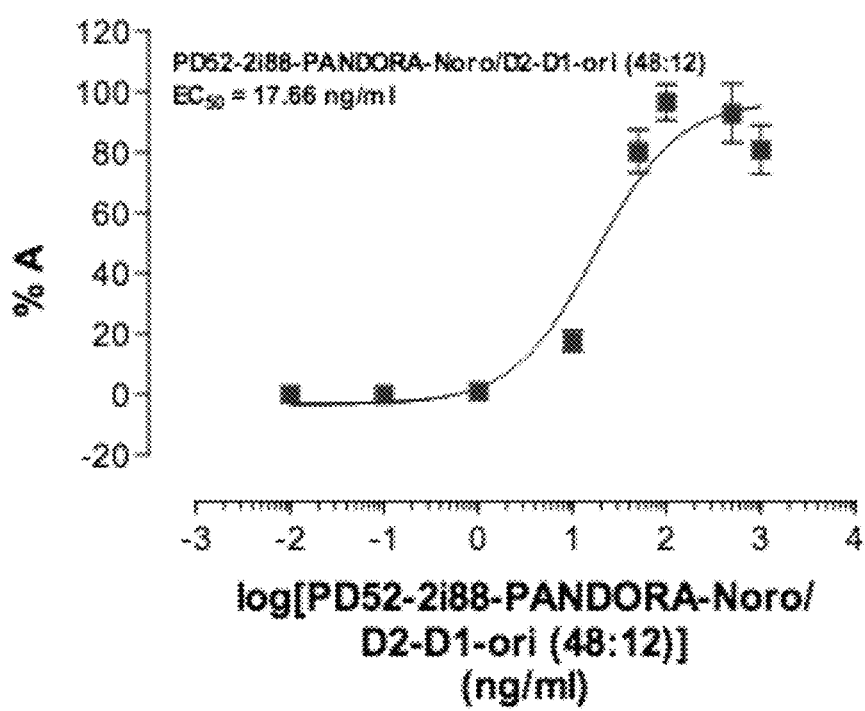

FIGS. 7(A)-7(C): Activation of the TLR5 cellular pathway.

Figure 8:
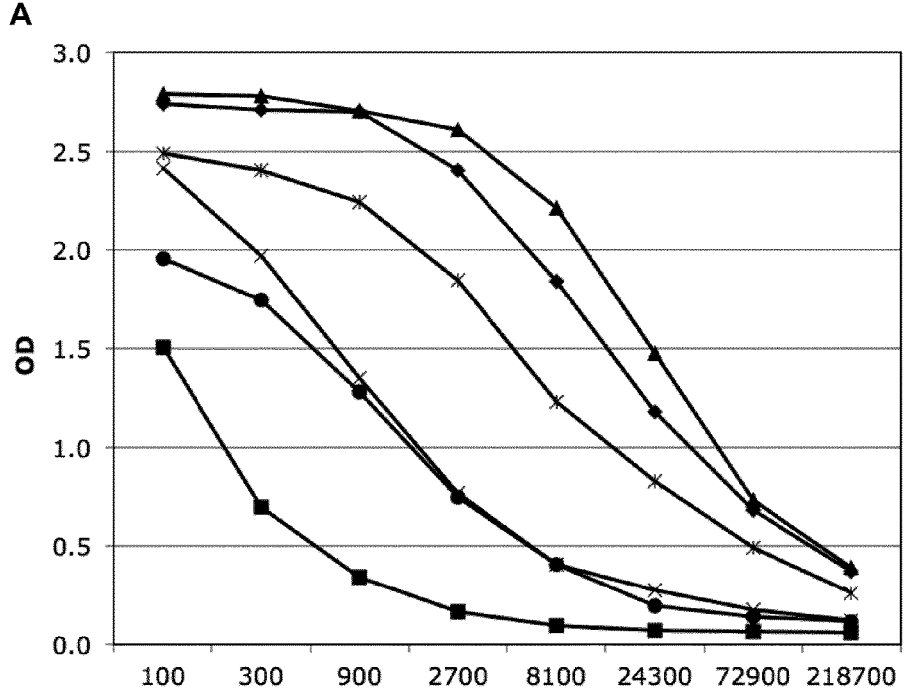
Figure 8:
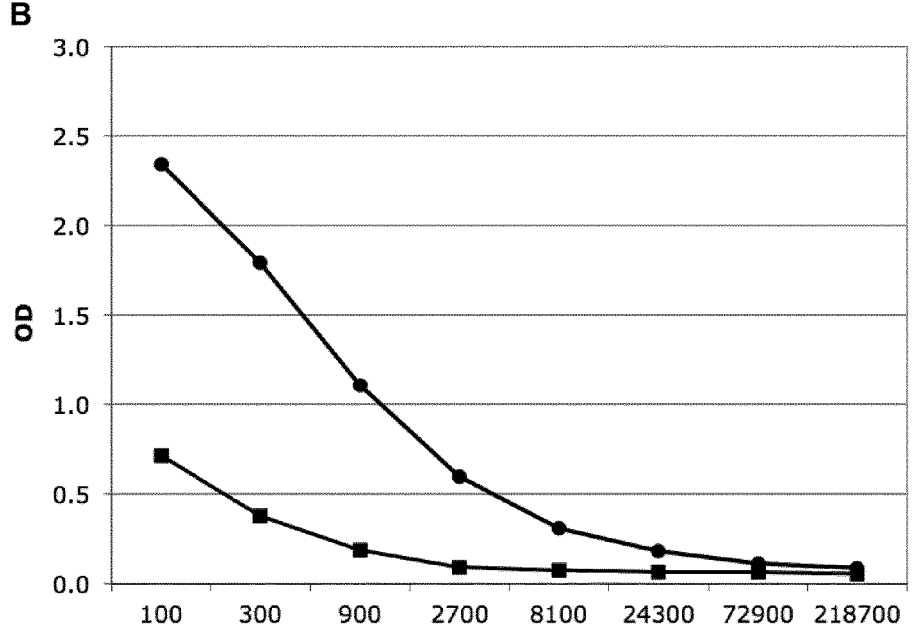

FIG. 7(A) Long-D2-D1-ori (Example 5)
FIG. 7(B) T81c-WRW-8RRVRA-D0-D1: T81c-WRW-8RRVRA-T1BT* (12:48) (Example 6)
FIG. 7(C) PD52-2i88-PANDORA-D2-D1-ori: PD52-2i88-PANDORA-Noro (5:55) (Example 7)
Upper panels: Dose-responsive activity evaluation
Lower panels: EC50 evaluation
IMG-2205: *Salmonella typhimurium* flagellin (0.29 ng/ml), positive control.
X-axis: concentration (ng/ml) of the nanoparticle.
Y-axis: SEAP expression (ng/ml) or % A=% activity FIG. 8: ELISA binding analysis of antibody titers after immunization in C57Bl/6 mice (described in Examples 8 [panel A] and 9 [panel B]).

A)
■ T81c-8-Pf alone at a dose of 1 µg
♦ T81c-8-Pf alone at a dose of 10 µg
X Co-assembly of T81c-8-D0-D1 and T81c-8-Pf at a ratio of 3:57 and a dose of 1 µg
▲ Co-assembly of T81c-8-D0-D1 and T81c-8-Pf at a ratio of 3:57 and a dose of 10 µg
● Co-assembly of T81c-8-D0-D1 and T81c-8-Pf at a ratio of 9:51 and a dose of 1 µg)

✳ Co-assembly of T81c-8-D0-D1 and T81c-8-Pf at a ratio of 9:51 and a dose of 10 µg X-axis: dilution factor of the serum Y-axis: OD=optical density ELISA plate is coated with the full immunogen used for immunization

B)

Figure 9:
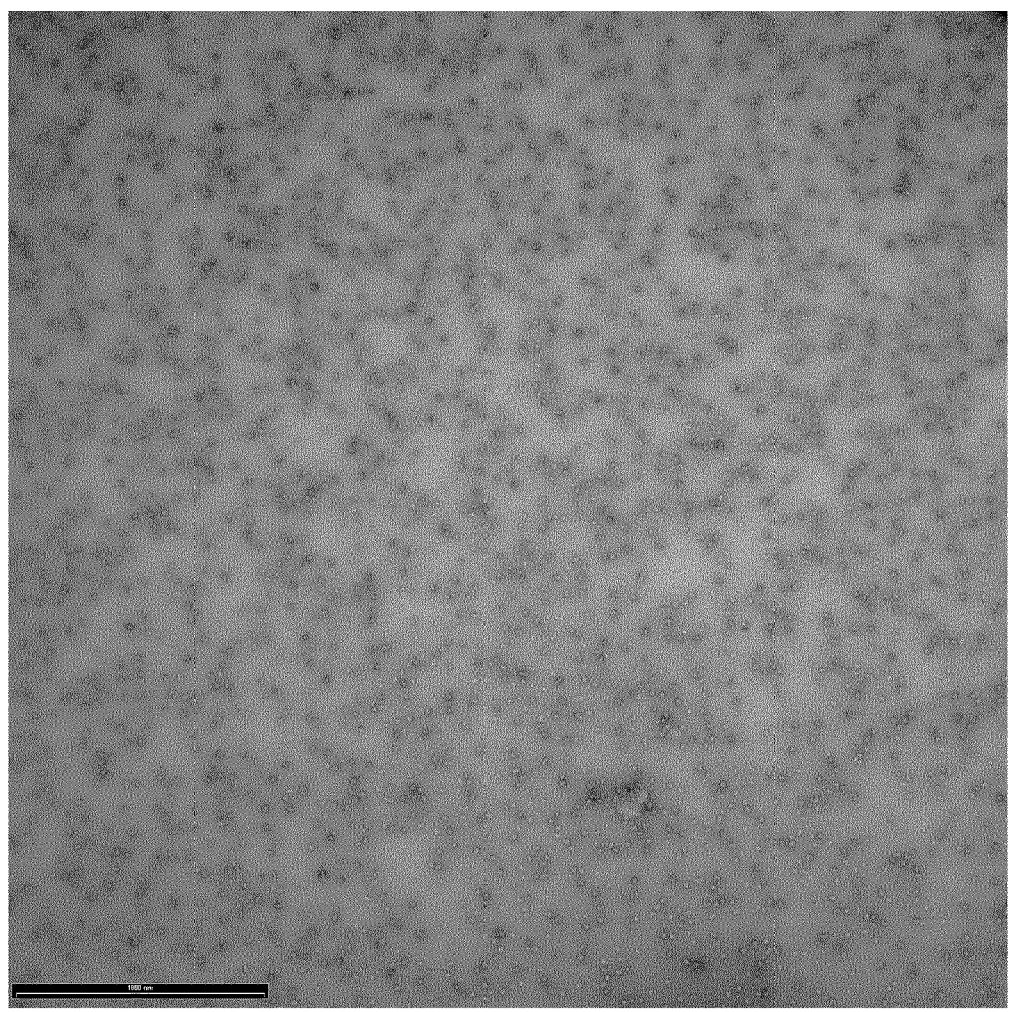

Co-assembly of DIM-D0-D1 and DIM-D2-D1-tip3_NIC-pept at a ratio of 5:55 and a dose of 10 µg ■ Nicotine coupled to the carrier KLH at a dose of 10 µg X-axis: Dilution factor of the serum Y-axis: OD=optical density ELISA plate is coated only with nicotine attached to an unrelated carrier FIG. 9: Transmission electron micrographs of protein nanoparticles of the construct Nic-DEDDL.

After refolding and co-assembly of recombinantly expressed protein, the nanoparticle was adsorbed on carbon-coated grids and negatively stained with 2% uranyl acetate.

The bar represents 1000 nm

Figure 10:
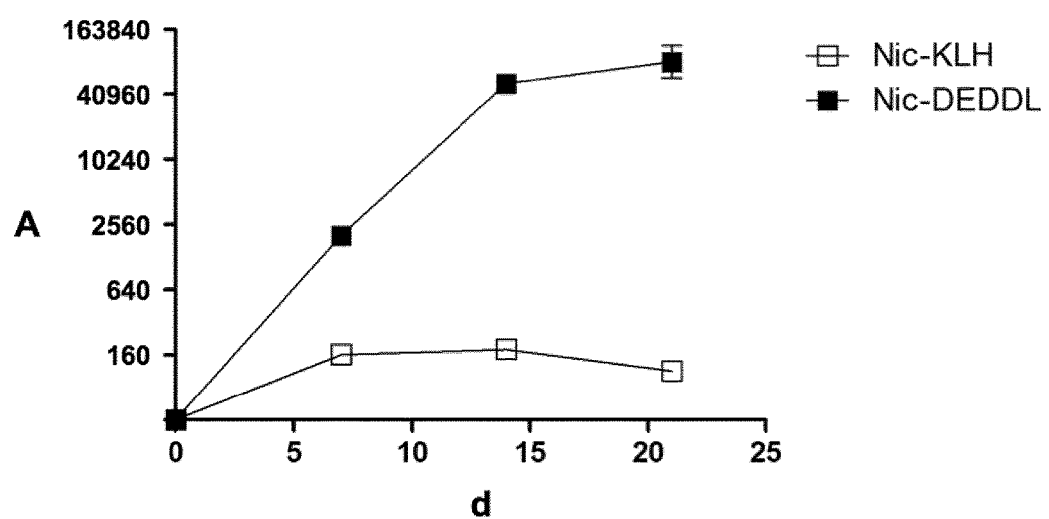

FIG. 10: Antibody formation

Groups of three C57Bl/6 mice were immunized s.c. with either 10 µg of Nic-DEDDL (Example 10) or 10 µg of Nic-KLH (nicotine coupled to carrier KLH) as a positive control in three injections each one week apart. The antibody titer at day 0 (i.e. before the first injection) and then one week after each injection has been determined by ELISA. d=days after first immunization; A=antibody titer ($\log_2$ scale).

DETAILED DESCRIPTION OF THE INVENTION

In the present invention different forms of flagellin that incorporate different domains of flagellin in either orientation incorporated into the nanoparticles are described. Some of the designs have flagellin attached to the nanoparticles with their N- and C-terminal end close to the nanoparticle surface (FIGS. 1(A)-1(E)), while in other designs the distant portions of flagellin are close to the nanoparticle surface, hence presenting flagellin in the opposite orientation on the nanoparticles (FIGS. 2(A)-2(B)).

Since inflammatory immune responses are one of the main problems of adjuvants, and in particular of TLR binding adjuvants, it is beneficial to reduce their potential to induce inflammatory responses. It is known that the C-terminal portion of flagellin, which is part of the D0 domain, contains a peptide sequence that interacts with the inflammasome and hence is responsible for the inflammatory reactions of flagellin. Therefore flagellin constructs that lack the C-terminal portion of the D0 domain that activates the inflammasome have been engineered (FIGS. 2(A)-2(B)).

The invention relates to a self-assembling protein nanoparticle consisting of aggregates of a multitude of building blocks of formula (Ia) or (Ib)

X-ND1-L1-ND2-FLA    (Ia)

or

FLA-ND1-L1-ND2-X    (Ib), consisting of a continuous chain comprising a protein oligomerization domain ND1, a linker L1, a protein oligomerization domain ND2, a derivative of flagellin FLA, and a further substituent X, wherein ND1 is a protein that forms oligomers $(ND1)_m$ of m subunits ND1, ND2 is a protein that forms oligomers $(ND2)_n$ of n subunits ND2, m and n each is a figure between 2 and 10, with the proviso that m is not equal n and not a multiple of n, and n is not a multiple of m, L1 is a bond or a short flexible linker, FLA is flagellin, or a derivative of flagellin lacking parts of the flagellin amino acid sequence but at least containing the TLR5 binding domain D1, and wherein optionally the missing domain(s) are replaced by a flexible linker segment of 1 to 20 amino acids joining the two ends of the remaining flagellin sequence, or are replaced by a fully folded protein antigen;

X is absent or a peptide or protein sequence comprising 1 to 1000 amino acids, optionally co-assembled with a multitude of building blocks of the formula (II)

Y-ND3-L2-ND4-Z    (II), consisting of a continuous chain comprising a protein oligomerization domain ND3, a linker L2, a protein oligomerization domain ND4, and further substituents Y and Z, wherein ND3 is a protein that forms oligomers $(ND3)_y$ of y subunits ND3, ND4 is a protein that forms oligomers $(ND4)_z$ of z subunits ND4, y and z each is a figure between 2 and 10, with the proviso that y is not equal z and not a multiple of z, and z is not a multiple of y, and wherein either ND3 is identical to ND1, or ND4 is identical to ND2, or both ND3 and ND4 are identical to ND1 and ND2, respectively, L2 is a bond or a short flexible linker that may be different from L1 or identical to L1, and Y and Z are, independently of each other, absent or a peptidic sequence of 1 to 100 amino acid comprising 1 to 1000 amino acids.

The protein nanoparticles of this invention offer a very elegant way to co-localize the adjuvant molecule with the immunogen of interest, hence the adjuvant property of flagellin can be co-localized with the vaccine antigen against which an immune response is desired. By co-assembly of two nanoparticle-forming protein chains, one with flagellin or with a flagellin derivative (FLA) in a molecule of formula (Ia) or (Ib), the other one of formula (II) incorporating the antigen of interest (Y or Z), into one single protein nanoparticle, the adjuvant and the antigen are perfectly co-localized. Hence in these designs the adjuvant effect is co-localized with the benefit of the repetitive antigen display of the nanoparticles. Furthermore, the contribution of the adjuvant effect can be increased or decreased by using different co-assembly ratios of flagellin-containing protein chains of formula (Ia) or (Ib) with antigen-containing protein chains of formula (II). The adjuvant effect is tailored in order to optimize between best antigenicity and lowest side effect.

As set out above, FLA is flagellin or a derivative of flagellin lacking parts of the flagellin amino acid sequence but at least containing the TLR5 binding domain D1. The missing domain(s) may be substituted by a flexible linker segment of 1 to 20 amino acids joining the two ends of the remaining flagellin sequence, or they may be replaced by a fully folded protein antigen. The flexible linker region may contain suitable attachment sites for the covalent coupling of antigens.

The flagellin-containing nanoparticles by themselves (i.e. without co-assembly with an antigen-containing nanoparticle-forming protein chain) can be used as a conventional adjuvant that is simply added to any form of antigen delivery in a given vaccine.

As a further alternative option, antigens can be engineered as substituent X onto the flagellin-only containing nanoparticle-forming protein chains of formula (Ia) or (Ib), i.e. again without co-assembly with an antigen-containing nanoparticle-forming protein chain of formula (II), in order to maximize the benefits from the adjuvant effect and the repetitive antigen display effect, using an antigen X as a B-cell epitope and the flagellin derivative FLA as adjuvant.

Since in the architecture of flagellin the protein chain is running as a loop through all domains D0, D1, D2 and D3 and back again, one or several domains may be removed from the sequence by rejoining the two ends into a continuous peptide chain resulting in a flagellin derivative FLA. Thus, a flagellin derivative construct lacking the D2 and D3 domains of flagellin can easily be engineered, simply by connecting the protein chain at the interface of the D1 and D2 domains. Similar, the tip domains (either D3, or D2 and D3 together) can be replaced by a protein antigen, provided this protein antigen with its N- and C-termini can be connected to the N- and C-termini at the interface between D1 and D2. The tip domains D2 and D3 can also be replaced by a peptide sequence with suitable residues for the covalent coupling of antigen molecules. An example of such a peptide loop is the sequence KYKDGDKGDDK (SEQ ID NO:1), which contains four lysine residues for the covalent coupling to its primary amino group. Such a hydrophilic loop incorporating lysine residues provides coupling sites for the covalent attachment of ligand molecules to the primary amino acid of the side chain of lysine. Replacing the lysine residues within the flagellin sequence by arginine removes unwanted coupling sites in the rest of the molecule. These two modifications give a flagellin derivative with the following sequence:

(SEQ ID NO: 28)
MAQVINTNSLSLLTQNNLNRSQSALGTAIERLSSGLRINSARDDAAGQAI
ANRFTANIRGLTQASRNANDGISIAQTTEGALNEINNNLQRVRELAVQSA
NSTNSQSDLDSIQAEITQRLNEIDRVSGQTQFNGVRVLAQDNTLTIQVGA
NDGETIDIDLRQINSQTLGLDQLNVQQKYKDGDKGDDKTENPLQRIDAAL
AQVDALRSDLGAVQNRFNSAITNLGNTVNNLSEARSRIEDSDYATEVSNM
SRAQILQQAGTSVLAQANQVPQNVLSLLR

It is a further scope of this invention to engineer flagellin as a dimer onto the nanoparticle. Thus, the interaction with TLR5, which is also a dimer, is optimized. This is easily accomplished by using a dimeric protein oligomerization domain as ND1 (m is 2) or ND2 (n is 2) and use it as attachment site for the flagellin derivative FLA, i.e. as shown in formula (Ib) or (Ia), respectively. This will force the flagellin derivative into a dimeric form, which more readily interacts with TLR5 (FIGS. 2(A)-2(B)). Preferably, in such a design the dimeric oligomerization domain in the building block of formula (Ia) or (Ib) to which flagellin is attached (either ND2 in formula (Ia) or ND1 in formula (Ib)) is different from the corresponding oligomerization domain in the building block of formula (II) (either ND4 when co-assembled with chains of formula (Ia), or ND3 when co-assembled with chains of formula (Ib)). Preferably the dimeric oligomerization domain in the building block of formula (Ia) or (Ib) has a stronger interaction, i.e. dimer forming potential, than the corresponding oligomerization domain (ND3 or ND4) in the building block of formula (II). This will guarantee that in a co-assembled nanoparticle with building blocks of formula (Ia) or (Ib) and formula (II) the flagellin or flagellin derivative FLA always forms a dimer on adjacent building blocks of formula (Ia) or (Ib) and is not distributed as a single monomer throughout the co-assembled nanoparticle.

Furthermore, by engineering flagellin in the flipped orientation, preferentially as a dimer, onto the nanoparticle, the interaction with the TLR5 dimer may be optimized (FIGS. 2(A)-2(B)). Such a nanoparticle is preferred. For example a D1-D2 flagellin construct can be engineered by joining the protein chains with a peptide sequence like KAKKKDGKDDKDS (SEQ ID NO:29, "T" in FIGS. 2(A)-2(B)) at the interface between the D0 and D1 domain, thus omitting domain D0, and removing the D3 domain completely without rejoining the protein chains. Consequently, the resulting flagellin molecule will have its N- and C-termini in the D2 domain to give a D2-D1 sequence like (SEQ ID NO: 30)
SARLSDLEANNAVRGESKITVNGAEYTANATGDRITLAGRTMFIDRTASG
VSTLINEDAAAARRSTANPLASIDSALSRVDAVRSSLGAIQNRFDSAKAK
KKDGKDDKDSKNANDGISIAQTTEGALNEINNNLQRVRELSVQATNGTNS
DSDLRSIQDEIQQRLEEIDRVSNQTQFNGVKVLSQDNQMKIQVGAKDGET
ITIDLQKIDVKSLGLDGFNVNGPREATVGDLRSSFRNVTGYDTYAAGADR
YRVDINSGAV Similar flexible linker sequences ("T" in FIGS. 2(A)-2(B)) with 1 to 20 amino acids could be used such as for example GS or GKDGKDGS (SEQ ID NO:31) or GKDGKDGKDGKDGS (SEQ ID NO:32). Preferably, linker sequences contain mainly charged or polar amino acids interspersed with glycine residues to make the linker flexible. To avoid unwanted coupling sites on this D2-D1 construct, lysine residues are replaces by arginine residues.

The flagellin derivative FLA has to then to be connected to a dimeric oligomerization domain ND1 or ND2 at the D2 part of flagellin. Preparing a nanoparticle from such a building block, either alone or co-assembled with a corresponding building block of formula (II), will form a preferred nanoparticle with a flagellin derivative in flipped orientation.

Monomeric Building Blocks

A peptide (or polypeptide or protein) is a chain or sequence of amino acids covalently linked by amide bonds. The peptide may be natural, modified natural, partially synthetic or fully synthetic. Modified natural, partially synthetic or fully synthetic is understood as meaning not occurring in nature. The term amino acid embraces both naturally occurring amino acids selected from the 20 essential natural α-L-amino acids, synthetic amino acids, such as α-D-amino acids, 6-aminohexanoic acid, norleucine, homocysteine, or the like, as well as naturally occurring amino acids which have been modified in some way to alter certain properties such as charge, such as phoshoserine or phosphotyrosine, or other modifications such as n-octanoyl-serine, or the like. In derivatives of amino acids the amino group forming the amide bond is alkylated, or a side chain amino, hydroxy or thio functions is alkylated or acylated, or a side chain carboxy function is amidated or esterified. Preferably a protein of the invention comprises amino acids selected from the 20 essential natural α-L-amino acids.

In a rough approximation peptides can be distinguished from proteins on the basis of their size, i.e. approximately a chain of 50 amino acids or less can be considered to be a peptide, while longer chains can be considered to be proteins. Dipeptides are the shortest peptides and consist of 2 amino acids joined by a single peptide bond. Likewise tripeptides consist of three amino acids, tetrapeptides consist of four amino acids, etc. A polypeptide is a long, continuous, and unbranched peptide chain. In the literature boundaries of the size that distinguish peptides from proteins are somewhat weak. Sometimes long "peptides" such as amyloid beta have been considered proteins, and vice versa smaller proteins such as insulin have been referred to as peptides.

A short flexible linker chain L1 or L2 is selected from optionally substituted carbon atoms, optionally substituted nitrogen atoms, oxygen atoms, sulfur atoms, and combinations thereof, with preferably 1 to 60 atoms, in particular 1 to 20 atoms in the chain. Such a short flexible linker chain is, e.g. a polyethylenoxy chain, a flexible sugar chain or, preferably, a flexible peptide chain, e.g. a peptide chain consisting of 1 to 20 amino acids, in particular 1 to 6 amino acids comprising one or several amino acids glycine. Most preferred linkers consist of 1 to 6 amino acids with a high content of glycine.

Oligomerization domains according to the invention are preferably coiled-coils. A coiled-coil is a protein sequence with a contiguous pattern of mainly hydrophobic residues spaced 3 and 4 residues apart, which assembles to form a multimeric bundle of helices, as will be explained in more detail hereinbelow.

Oligomerization domains, which are not coiled-coils, are, for example the trimerization domain (foldon) of the bacteriophage T4 protein fibritin (Tao, Y. et al., Structure 1997, 5:789-798)

Oligomerization domains ND1, ND2, ND3 and/or ND4, and linkers L1 and/or L2 may optionally be further substituted by targeting entities, or substituents reinforcing the adjuvant properties of the nanoparticle, such as an immunostimulatory nucleic acid, preferably an oligodeoxynucleotide containing deoxyinosine, an oligodeoxynucleotide containing deoxyuridine, an oligodeoxynucleotide containing a CG motif, CpGs, imiquimod, resiquimod, gardiquimod, an inosine and cytidine containing nucleic acid molecule, or the like. Other substituents reinforcing the adjuvant properties of the nanoparticle are antimicrobial peptides, such as cationic peptides, which are a class of immunostimulatory, positively charged molecules that are able to facilitate and/or improve adaptive immune responses. An example of such a peptide with immunopotentiating properties is the positively charged artificial antimicrobial peptide KLKLLLLLKLK (SEQ ID NO:2) which induces potent protein-specific type-2 driven adaptive immunity after prime-boost immunizations. A particular targeting entity considered as substituent is an ER-targeting signal, i.e. a signal peptide that induces the transport of a protein or peptide to the endoplasmic reticulum (ER).

Optional substituents, e.g. those optional substituents described hereinabove, are preferably connected to suitable amino acids close to the end and opposite to the end bound to L1 or L2 of the oligomerization domain ND1, ND2, ND3 and/or ND4. On self-assembly of the protein nanoparticle, such substituents will then be presented at the surface of the nanoparticle. Such substituents may be connected to the end of the continuous protein chain, or may be connected to a side chain functional group of an amino acid located near the end of ND1, ND2, ND3 and/or ND4 opposite to the end bound to L1 or L2.

In a most preferred embodiment the substituent is a peptide or protein substituent and is termed X, Y and/or Z representing a simple extension of the protein chain, e.g. as X-ND1-L1-ND2-FLA at the N-terminal end of ND1, or at both ends as Y-ND3-L2-ND4-Z to generate a combined single continuous protein sequence, which may be expressed in a recombinant protein expression system as one single molecule.

In other embodiments a peptidic or non-peptidic substituent may be connected to a side chain functional group of an amino acid located near the end of ND1, ND2, ND3 and/or ND4 opposite to the end bound to L1 or L2, or preferably to a side chain functional group of an amino acid within the extensions X, Y and/or Z if X, Y and/or Z are peptides or proteins.

It is also possible to attach a substituent to the linker L1 or L2. In such case, upon refolding of the self-assembling protein nanoparticle, the substituent will be located in the inner cavity of the self-assembling protein nanoparticle.

A tendency to form oligomers means that such proteins can form oligomers depending on the conditions, e.g. under denaturing conditions they are monomers, while under physiological conditions they may form, for example, dimers, trimers, tetramers or pentamers. Under predefined conditions they adopt one single oligomerization state, which is needed for nanoparticle formation. However, their oligomerization state may be changed upon changing conditions, e.g. from dimers to trimers upon increasing salt concentration (Burkhard P. et al., Protein Science 2000, 9:2294-2301) or from pentamers to monomers upon decreasing pH.

A building block architecture according to formula (Ia), (Ib) or (II) is clearly distinct from viral capsid proteins. Viral capsids are composed of either one single protein, which forms oligomers of 60 or a multiple thereof, as e.g. the hepatitis virus B particles (EP 1 262 555, EP 0 201 416), or of more than one protein, which co-assemble to form the viral capsid structure, which can adopt also other geometries apart from icosahedra, depending on the type of virus (Fender P. et al., Nature Biotechnology 1997, 15:52-56). Self-assembling protein nanoparticles (SAPN) of the present invention are also clearly distinct from virus-like particles, as they (a) are constructed from other than viral capsid proteins and (b) that the cavity in the middle of the nanoparticle is too small to accommodate the DNA/RNA of a whole viral genome.

Protein oligomerization domains are well-known (Burkhard P. et al., Trends Cell Biol 2001, 11:82-88). The RCSB-PDB protein structure database (http://www.rcsb.org/) contains atomic structures of proteins. This website offers tools to identify protein oligomers among those atomic structures. Using the advanced search mode (http://www.rsb.org/pdb/search/advSearch.do) with the qualifier "A5" in "Protein Stoichiometry" retrieves pentameric protein oligomerizations domains. Using the advanced search mode with the qualifier "Coiled coil proteins" in "SCOP classification Browser" retrieves coiled-coil protein oligomerizations domains. Combining the two searches retrieves all pentameric coiled-coil protein structures in the database. Likewise, dimeric, trimeric or tetrameric coiled-coil structures can be retrieved using "A2", "A3" or "A4" as qualifiers, respectively. In the present invention the oligomerization domains ND1, ND2, ND3 and ND4 are preferably coiled-coil domains. A coiled coil is a protein sequence with a contiguous pattern of mainly hydrophobic residues spaced 3 and 4 residues apart, usually in a sequence of seven amino acids (heptad repeat) or eleven amino acids (undecad repeat), which assembles (folds) to form a multimeric bundle of helices. Coiled coils with sequences including some irregular distribution of the 3 and 4 residues spacing are also contemplated. Hydrophobic residues are in particular the hydrophobic amino acids Val, Ile, Leu, Met, Tyr, Phe and Trp. Mainly hydrophobic means that at least 50% of the residues must be selected from the mentioned hydrophobic amino acids.

For example, in a preferred monomeric building block of formula (Ia), (Ib) or (II), ND1, ND2, ND3 and ND4 are proteins of any of the formulae

[aa(a)-aa(b)-aa(c)-aa(d)-aa(e)-aa(f)-aa(g)]$_x$     (IIIa),

[aa(b)-aa(c)-aa(d)-aa(e)-aa(f)-aa(g)-aa(a)]$_x$     (IIIb),

[aa(c)-aa(d)-aa(e)-aa(f)-aa(g)-aa(a)-aa(b)]$_x$     (IIIc),

[aa(d)-aa(e)-aa(f)-aa(g)-aa(a)-aa(b)-aa(c)]$_x$     (IIId),

[aa(e)-aa(f)-aa(g)-aa(a)-aa(b)-aa(c)-aa(d)]$_x$     (IIIe),

[aa(f)-aa(g)-aa(a)-aa(b)-aa(c)-aa(d)-aa(e)]$_x$     (IIIf),

[aa(g)-aa(a)-aa(b)-aa(c)-aa(d)-aa(e)-aa(f)]$_x$     (IIIg), wherein aa means an amino acid or a derivative thereof, aa(a), aa(b), aa(c), aa(d), aa(e), aa(f), and aa(g) are the same or different amino acids or derivatives thereof, preferably aa(a) and aa(d) are the same or different hydrophobic amino acids or derivatives thereof; and x is a figure between 2 and 20, preferably between 3 and 10.

A heptad is a heptapeptide of the formula aa(a)-aa(b)-aa(c)-aa(d)-aa(e)-aa(f)-aa(g) (IIIa) or any of its permutations of formulae (IIIb) to (IIIg).

Preferred are monomeric building blocks of formula (Ia), (Ib) or (II) wherein all protein oligomerization domains ND1, ND2, ND3 and ND4 are (1) a protein of any of the formulae (IIIa) to (IIIg) wherein x is 3, and aa(a) and aa(d) are selected from the 20 natural α-L-amino acids such that the sum of scores from Table 1 for these 6 amino acids is at least 14, and such proteins comprising up to 17 further heptads; or (2) a protein of any of the formulae (IIIa) to (IIIg) wherein x is 3, and aa(a) and aa(d) are selected from the 20 natural α-L-amino acids such that the sum of scores from Table 1 for these 6 amino acids is at least 12, with the proviso that one amino acid aa(a) is a charged amino acid able to form an inter-helical salt bridge to an amino acid aa(d) or aa(g) of a neighboring heptad, or that one amino acid aa(d) is a charged amino acid able to form an inter-helical salt bridge to an amino acid aa(a) or aa(e) of a neighboring heptad, and such proteins comprising up to two further heptads. A charged amino acid able to form an inter-helical salt bridge to an amino acid of a neighboring heptad is, for example, Asp or Glu if the other amino acid is Lys, Arg or His, or vice versa.

TABLE 1

Scores of amino acid for determination of preference

| Amino acid | Position aa (a) | Position aa (d) |
| --- | --- | --- |
| L (Leu) | 3.5 | 3.8 |
| M (Met) | 3.4 | 3.2 |
| I (Ile) | 3.9 | 3.0 |

TABLE 1-continued

Scores of amino acid for determination of preference

| Amino acid | Position aa (a) | Position aa (d) |
| --- | --- | --- |
| Y (Tyr) | 2.1 | 1.4 |
| F (Phe) | 3.0 | 1.2 |
| V (Val) | 4.1 | 1.1 |
| Q (Gln) | −0.1 | 0.5 |
| A (Ala) | 0.0 | 0.0 |
| W (Trp) | 0.8 | −0.1 |
| N (Asn) | 0.9 | −0.6 |
| H (His) | −1.2 | −0.8 |
| T (Thr) | 0.2 | −1.2 |
| K (Lys) | −0.4 | −1.8 |
| S (Ser) | −1.3 | −1.8 |
| D (Asp) | −2.5 | −1.8 |
| E (Glu) | −2.0 | −2.7 |
| R (Arg) | −0.8 | −2.9 |
| G (Gly) | −2.5 | −3.6 |
| P (Pro) | −3.0 | −3.0 |
| C (Cys) | 0.2 | −1.2 |

Also preferred are monomeric building blocks of formula (Ia), (Ib) or (II) wherein one or more protein oligomerization domains ND1, ND2, ND3 or ND4 are selected from the following preferred proteins:

(11) Protein of any of the formulae (IIIa) to (IIIg) wherein aa(a) is selected from Val, Ile, Leu and Met, and a derivative thereof, and aa(d) is selected from Leu, Met, Val and Ile, and a derivative thereof.

(12) Protein of any of the formulae (IIIa) to (IIIg) wherein one aa(a) is Asn and the other aa(a) are selected from Asn, Ile and Leu, and aa(d) is Leu. Such a protein is usually a dimerization domain.

(13) Protein of any of the formulae (IIIa) to (IIIg) wherein aa(a) and aa(d) are both Leu or both Ile. Such a protein is usually a trimerization domain.

(14) Protein of any of the formulae (IIIa) to (IIIg) wherein aa(a) and aa(d) are both Trp. Such a protein is usually a pentamerization domain.

(15) Protein of any of the formulae (IIIa) to (IIIg) wherein aa(a) and aa(d) are both Phe. Such a protein is usually a tetramerization domain.

(16) Protein of any of the formulae (IIIa) to (IIIg) wherein aa(a) and aa(d) are both either Trp or Phe. Such a protein is usually a pentamerization domain.

(17) Protein of any of the formulae (IIIa) to (IIIg) wherein aa(a) is either Leu or Ile, and one aa(d) is Gln and the other aa(d) are selected from Gln, Leu and Met. Such a protein has the potential to be a pentamerization domain.

Other preferred proteins are proteins (1), (2), (11), (12), (13), (14), (15), (16) and (17) as defined hereinbefore, and wherein further

(21) at least one aa(g) is selected from Asp and Glu and aa(e) in a following heptad is Lys, Arg or His; and/or

(22) at least one aa(g) is selected from Lys, Arg and His, and aa(e) in a following heptad is Asp or Glu, and/or

(23) at least one aa(a to g) is selected from Lys, Arg and His, and an aa(a to g) 3 or 4 amino acids apart in the sequence is Asp or Glu. Such pairs of amino acids aa(a to g) are, for example aa(b) and aa(e) or aa(f).

Coiled-coil prediction programs such as PCOILS (http://toolkit.tuebingen.mpg.de/pcoils; Gruber M. et al., J. Struct. Biol. 2006, 155(2): 140-5) or MULTICOIL (http://groups.c-sail.mit.edu/cb/multicoil/cgi-bin/multicoil.cgi) can predict coiled-coil forming protein sequences. Therefore, in a monomeric building block of formula (Ia), (Ib) or (II), ND1, ND2, ND3 and ND4 are proteins that contain at least a sequence two heptad-repeats long that is predicted by the coiled-coil prediction program PCOILS to form a coiled-coil with higher probability than 0.9 for all its amino acids with at least one of the window sizes of 14, 21, or 28.

In a more preferred monomeric building block of formula (Ia), (Ib) or (II), ND1, ND2, ND3 and ND4 are proteins that contain at least one sequence three heptad-repeats long that is predicted by the coiled-coil prediction program PCOILS to form a coiled-coil with higher probability than 0.9 for all its amino acids with at least one of the window sizes of 14, 21, or 28.

In another more preferred monomeric building block of formula (Ia), (Ib) or (II), ND1, ND2, ND3 and ND4 are proteins that contain at least two separate sequences two heptad-repeats long that are predicted by the coiled-coil prediction program PCOILS to form a coiled-coil with higher probability than 0.9 for all its amino acids with at least one of the window sizes of 14, 21, or 28.

Known coiled-coil sequences may be retrieved from data banks such as the RCSB protein data bank (http://www.rcsb.org).

Most preferred are the coiled-coil sequences and monomeric building blocks described in the examples.

In yet another preferred embodiment, one oligomerization domain ND1, ND2, ND3 or ND4 is the trimerization domain (foldon) of the bacteriophage T4 protein fibritin (Tao, Y. et al., Structure 1997, 5:789-798) or a derivative thereof. This trimerization domain has the sequence GYIPEAPRDGQAYVRKDGEWVLLSTFL (SEQ ID NO:3). Small modifications of this domain are also envisaged.

Self-Assembling Protein Nanoparticles: LCM Units

Self-assembling protein nanoparticles (SAPN) are formed from monomeric building blocks of formula (Ia), (Ib) or mixtures of monomeric building blocks of formula (Ia) or (Ib) with monomeric building blocks of formula (II). If such building blocks assemble, they will form so-called "LCM units". The number of monomeric building blocks, which will assemble into such an LCM unit will be defined by the least common multiple (LCM). Hence, if for example the oligomerization domains of the monomeric building block form a pentamer $(ND1)_5$ (m=5) and a dimer $(ND2)_2$ (n=2), 10 monomers will form an LCM unit. If the linker segment L has the appropriate length, this LCM unit may assemble in the form of a spherical protein nanoparticle.

Self-assembling protein nanoparticles (SAPN) may be formed by the assembly of only one or more than one LCM units (Table 2). Such SAPN represent topologically closed structures.

Regular Polyhedra

There exist five regular polyhedra, the tetrahedron, the cube, the octahedron, the dodecahedron and the icosahedron. They have different internal rotational symmetry elements. The tetrahedron has a 2-fold and two 3-fold axes, the cube and the octahedron have a 2-fold, a 3-fold and a 4-fold rotational symmetry axis, and the dodecahedron and the icosahedron have a 2-fold, a 3-fold and a 5-fold rotational symmetry axis. In the cube the spatial orientation of these axes is exactly the same as in the octahedron, and also in the dodecahedron and the icosahedron the spatial orientation of these axes relative to each other is exactly the same. Hence, for the purpose of SAPN of the invention the dodecahedron and the icosahedron can be considered to be identical. The dodecahedron/icosahedron is built up from 60 identical three-dimensional building blocks (Table 2). These building blocks are the asymmetric units (AUs) of the polyhedron. They are pyramids and the pyramid edges correspond to one of the rotational symmetry axes, hence these AUs will carry at their edges 2-fold, 3-fold, and 5-fold symmetry elements. If these symmetry elements are generated from protein oligomerization domains such AUs are constructed from monomeric building blocks as described above. It is sufficient to align the two oligomerization domains ND1 and ND2, or ND3 and ND4 along two of the symmetry axes of the AU. If these two oligomerization domains form stable oligomers, the symmetry interface along the third symmetry axis will be generated automatically, and it may be stabilized by optimizing interactions along this interface, e.g. hydrophobic, hydrophilic or ionic interactions, or covalent bonds such as disulfide bridges.

TABLE 2

Possible combinations of oligomerization states in the formation of regular polyhedra

| ID No. | m | n | Polyhedron Type | LCM | No. of Even Units | No. of Building Blocks |
|---|---|---|---|---|---|---|
| 1 | 5 | 2 | dodecahedron/icosahedrons | 10 | 6 | 60 |
| 2 | 5 | 3 | dodecahedron/icosahedrons | 15 | 4 | 60 |
| 3 | 4 | 3 | cube/octahedron | 12 | 2 | 24 |
| 4 | 3 | 4 | cube/octahedron | 12 | 2 | 24 |
| 5 | 3 | 5 | dodecahedron/icosahedrons | 15 | 4 | 60 |
| 6 | 2 | 5 | dodecahedron/icosahedrons | 10 | 6 | 60 |
| 7 | 5 | 4 | Irregular | 20 | 1 | 20 |
| 8 | 4 | 5 | Irregular | 20 | 1 | 20 |

Assembly to Self-Assembling Protein Nanoparticles (SAPN) with Regular Polyhedral Symmetry To generate self-assembling protein nanoparticles (SAPN) with a regular geometry (dodecahedron, icosahedron, octahedron, cube), more than one LCM unit is needed. E.g. to form an icosahedron from a monomer containing trimeric and pentameric oligomerization domains, 4 LCM units, each composed of 15 monomeric building blocks are needed, i.e. the protein nanoparticle with regular geometry will be composed of 60 monomeric building blocks. The combinations of the oligomerization states of the two oligomerization domains needed and the number of LCM units to form the two possible polyhedra are listed in Table 2.

Whether the LCM units will further assemble to form regular polyhedra composed of more than one LCM unit depends on the geometrical alignment of the two oligomerizations domains ND1 and ND2, or ND3 and ND4 with respect to each other, especially on the angle between the rotational symmetry axes of the two oligomerization domains. This is mainly governed by i) the interactions between neighboring domains in a nanoparticle, ii) the length of the linker segment L, iii) the shape of the individual oligomerization domains. This angle is larger in the LCM units compared to the arrangement in a regular polyhedron. Also this angle is not identical in monomeric building blocks as opposed to the regular polyhedron. If this angle is restricted to the smaller values of the regular polyhedron (by means of attractive hydrophobic, hydrophilic or ionic interactions, or a covalent disulfide bridge between the two oligomerization domains) and the linker segment L is short enough, a given number of LCM units each containing a defined number of monomeric building blocks will then further anneal to form a regular polyhedron (Table 2), or enclose more monomeric building blocks to from nanoparticles lacking the strict internal symmetry of a polyhedron.

If the angle between the two oligomerization domains is sufficiently small (even smaller than in a regular polyhedron with icosahedral symmetry), then a large number (several hundred) protein chains can assemble into a protein nanoparticle. In such a design the SAPNs may have a molecular weight corresponding to several times 60 protein chains similar to the architectures described by the theory of quasi-equivalence or the tiling theory of viral capsids for "all-pentamer" virus architectures.

Preferably, antigens to be comprised in the flagellin-containing nanoparticles can be either B-cell epitopes and/or T-cell epitopes and are selected from the group consisting of (a) proteins or peptides suited to induce an immune response against cancer cells; (b) proteins, peptides or carbohydrates suited to induce an immune response against infectious diseases; (c) proteins or peptides suited to induce an immune response against allergens; (d) protein or peptide hormones suited to induce an immune response for the treatment of a human disease; and (e) hapten molecules suited to induce an immune response to treat addictions or other disorders. Protein nanoparticles comprising such proteins, peptidic fragments thereof, peptides, carbohydrates, or haptens may be suited to induce an immune response in humans, or also in farm animals and pets.

In a further aspect, the invention relates to monomeric building blocks of formula (Ia) or (Ib) as defined above.

In another aspect, the invention relates to composition comprising a protein nanoparticle as herein described. Such a composition is particularly suitable as a vaccine. Preferred vaccine compositions comprise the protein nanoparticle in an aqueous buffer solution, and may further comprise, for example, sugar derived excipients (such as glycerol, trehalose, sucrose, or the like) or amino acid derived excipients (such as arginine, proline, glutamate, or the like) or anionic, cationic, non-ionic or twitter-ionic detergents (such as cholate, deoxycholate, tween, or the like) or any kind of salt (such as NaCl, MgCl$_2$, or the like) to adjust the ionic strength of the solution.

In another aspect, the invention relates to a method of vaccinating a human or non-human animal, which comprises administering an effective amount of a protein nanoparticle as described hereinbefore to a subject in need of such vaccination.

Design of a FLA-SAPN (flagellin containing self-assembling protein nanoparticle)

A particular example of a FLA-SAPN according to the invention are the following constructs "FLA-SAPN-1a" and "FLA-SAPN-2".

T81c-WRW-8RRVRA-D0-D1 (FLJB_SALTY)(FLA-SAPN-1a) corresponding to formula (Ia)

```
                                                (SEQ ID NO: 4)
MGHHHHHHASWRWDGGLVPRGSWQTWNARWDQWSNDWNAWRSDWQAWRDD

WARWRALWMGGRLLLRLEELERRLEELERRLEELERFVAAWTLRVRALER

RLEELERRIEEIARGMAQVINTNSLSLLTQNNLNKSQSALGTAIERLSSG

LRINSAKDDAAGQAIANRFTANIKGLTQASRNANDGISIAQTTEGALNEI

NNNLQRVRELAVQSANSTNSQSDLDSIQAEITQRLNEIDRVSGQTQFNGV

KVLAQDNTLTIQVGANDGETIDIDLKQINSQTLGLDSLNVHGAPVDPASP

WTENPLQKIDAALAQVDALRSDLGAVQNRFNSAITNLGNTVNNLSEARSR

IEDSDYATEVSNMSRAQILQQAGTSVLAQANQVPQNVLSLLR
```

T81c-WRW-8RRVRA-T1 BT* (FLA-SAPN-2), corresponding to formula (II)

```
                                                (SEQ ID NO: 5)
MGHHHHHHASEYLNKIQNSLSTEWSPSSVTGSWQTWNARWDQWSNDWNAW

RSDWQAWRDDWARWRALWMGGRLLLRLEELERRLEELERRLEELERFVAA

WTLRVRALERRLEELERRIEEIARGSGDPNANPNVDPNANPNVNANPNAN

PNANP
```

Such constructs are composed of the following partial structures:

X

```
                                                (SEQ ID NO: 6)
MGHHHHHHASWRWDGGLVPRGS
```

ND1

```
                                                (SEQ ID NO: 7)
WQTWNARWDQWSNDWNAWRSDWQAWRDDWARWRALWM
```

L1
GG

ND2

```
                                                (SEQ ID NO: 8)
RLLLRLEELERRLEELERRLEELERFVAAWTLRVRALERRLEELERRIEE

IARG
```

FLA

```
                                                (SEQ ID NO: 9)
MAQVINTNSLSLLTQNNLNKSQSALGTAIERLSSGLRINSAKDDAAGQAI

ANRFTANIKGLTQASRNANDGISIAQTTEGALNEINNNLQRVRELAVQSA

NSTNSQSDLDSIQAEITQRLNEIDRVSGQTQFNGVKVLAQDNTLTIQVGA

NDGETIDIDLKQINSQTLGLDSLNVHGAPVDPASPWTENPLQKIDAALAQ

VDALRSDLGAVQNRFNSAITNLGNTVNNLSEARSRIEDSDYATEVSNMSR

AQILQQAGTSVLAQANQVPQNVLSLLR
```

Y

```
                                                (SEQ ID NO: 10)
MGHHHHHHASEYLNKIQNSLSTEWSPSSVTGS
```

ND3

```
                                                (SEQ ID NO: 7)
WQTWNARWDQWSNDWNAWRSDWQAWRDDWARWRALWM
```

L2
GG

ND4

```
                                                (SEQ ID NO: 8)
RLLLRLEELERRLEELERRLEELERFVAAWTLRVRALERRLEELERRIEE

IARG
```

Z

```
                                                (SEQ ID NO: 11)
SGDPNANPNVDPNANPNVNANPNANPNANP
```

For ease of purification the FLA-SAPN-1a starts with the sequence X as defined in formula (Ia) or (Ib):

```
                                                (SEQ ID NO: 6)
                         MGHHHHHHASWRWDGGLVPRGS
``` which contains a His-tag for nickel affinity purification and at the DNA level restriction sites for further sub-cloning (NcoI, NheI, BamHI).

For ND1a pentamerization domain was chosen (m=5). The particular pentameric coiled coil is a novel modification of the tryptophan-zipper pentamerization domain (Liu J. et al., Proc Natl Acad Sci USA 2004; 101(46):16156-61, pdb-entry 1T8Z).

The original tryptophan-zipper pentamerization domain has the sequence (SEQ ID NO: 12)
SSNAKWDQWSSDWQTWNAKWDQWSNDWNAWRSDWQAWKDDWARWNQRWDN

WAT.

The modified coiled-coil sequence of the pentamerization domain used for FLA-SAPN-1a starts at position 13, ends at position 49 and contains slight sequence variations at the C-terminal end (RALWM instead of NQRWD) but keeping the heptad repeat pattern of the tryptophane residues as in the original sequence (SEQ ID NO:12).

(SEQ ID NO: 7)
13-WQTWNARWDQWSNDWNAWRSDWQAWRDDWARWRALWM-49.

This sequence is extended then by the short linker L1 (GG) of two glycine residues, then connected with the trimerization domain ND2 of the following sequence, which is an extremely stable coiled-coil trimer:

(SEQ ID NO: 8)
RLLLRLEELERRLEELERRLEELERFVAAWTLRVRALERRLEELERRIEE

IARG

It has been shown that a trimer is formed even under completely denaturing conditions of an SDS-PAGE (FIG. 5). It also contains the pan-DR binding HTL-epitope string RFVAAWTLRVRA, which is a derivative of the PADRE sequence with optimized trimeric coiled-coil propensity.

In the FLA-SAPN-1a the portion "FLA" of formula 1a is composed of the D0 and D1 domains of *Salmonella typhimurium* flagellin (as in U.S. Pat. No. 8,420,102) with the following sequence (SEQ ID NO: 9)
MAQVINTNSLSLLTQNNLNKSQSALGTAIERLSSGLRINSAKDDAAGQAI

ANRFTANIKGLTQASRNANDGISIAQTTEGALNEINNNLQRVRELAVQSA

NSTNSQSDLDSIQAEITQRLNEIDRVSGQTQFNGVKVLAQDNTLTIQVGA

NDGETIDIDLKQINSQTLGLDSLNVHGAPVDPASPWTENPLQKIDAALAQ

VDALRSDLGAVQNRFNSAITNLGNTVNNLSEARSRIEDSDYATEVSNMSR

AQILQQAGTSVLAQANQVPQNVLSLLR

This design then results in the following sequence that was used for protein expression, purification and biophysical analysis:

(SEQ ID NO: 4)
MGHHHHHHASWRWDGGLVPRGSWQTWNARWDQWSNDWNAWRSDWQAWRDD

WARWRALWMGGRLLLRLEELERRLEELERRLEELERFVAAWTLRVRALER

RLEELERRIEEIARGMAQVINTNSLSLLTQNNLNKSQSALGTAIERLSSG

LRINSAKDDAAGQAIANRFTANIKGLTQASRNANDGISIAQTTEGALNEI

NNNLQRVRELAVQSANSTNSQSDLDSIQAEITQRLNEIDRVSGQTQFNGV

-continued

KVLAQDNTLTIQVGANDGETIDIDLKQINSQTLGLDSLNVHGAPVDPASP

WTENPLQKIDAALAQVDALRSDLGAVQNRFNSAITNLGNTVNNLSEARSR

IEDSDYATEVSNMSRAQILQQAGTSVLAQANQVPQNVLSLLR

A model of FLA-SAPN-1a monomer is shown in FIG. 10.

The corresponding construct "FLA-SAPN-2" is the following:

For ease of purification the FLA-SAPN-2 starts with the sequence Y as defined in formula (II)

(SEQ ID NO: 10)
MGHHHHHHASEYLNKIQNSLSTEWSPSSVTGS which contains a His-tag for nickel affinity purification, T-cell epitope sequence T1 BT* (Calvo-Calle J. M., Infection and immunity 2006:6929-6939) from the CS-protein of *plasmodium falciparum*

(SEQ ID NO: 13)
EYLNKIQNSLSTEWSPSSVT with one cysteine replaced by a serine and at the DNA level restriction sites for further sub-cloning (NcoI, NheI, BamHI) and hence is somewhat different from "X" of FLA-SAPN-1a.

ND3 in FLA-SAPN-2 is completely identical to ND1 in FLA-SAPN-1a to assure proper co-assembly.

(SEQ ID NO: 7)
13-WQTWNAKWDQWSNDWNAWRSDWQAWKDDWARWRALWM-49.

This sequence is extended then by the short linker L2 (GG) of two glycine residues, which is also identical to FLA-SAPN-1a.

In FLA-SAPN-2 the linker is then connected with the trimerization domain ND4 of the following sequence (SEQ ID NO: 8)
RLLLRLEELERRLEELERRLEELERFVAAWTLRVRALERRLEELERRIEE

IARG which is exactly the same as in FLA-SAPN-1a, hence the cores ND1-L1-ND2 and ND3-L2-ND4 and of the nanoparticles FLA-SAPN-1a and FLA-SAPN-2 are completely identical and assure proper co-assembly of the two protein chain upon refolding.

In the FLA-SAPN-2 the portion "Z" of formula (II) is composed of the repeat region of the circumsporozoite protein (CSP) of *Plasmodium falciparum*, which contains three repeats of (NANP) and some modifications thereof (DPNANPNVDPNANPNV, SEQ ID NO:14) that occur in the native CS-protein sequence and is the B-cell epitope, to which an immune response should be generated. It is linked to the particle by the sequence SG:

(SEQ ID NO: 11)
SGDPNANPNVDPNANPNVNANPNANPNANP

This design then results in the following sequence that was used for protein expression, purification and biophysical analysis:

(SEQ ID NO: 5)
MGHHHHHHASEYLNKIQNSLSTEWSPSSVTGSWQTWNARWDQWSNDWNAW

RSDWQAWRDDWARWRALWMGGRLLLRLEELERRLEELERRLEELERFVAA

WTLRVRALERRLEELERRIEEIARGSGDPNANPNVDPNANPNVNANPNAN

PNANP

A model of FLA-SAPN-2 monomer is shown in FIG. 1C.

A model of a nanoparticle co-assembled from FLA-SAPN-1a and FLA-SAPN-2 at a ratio of 1:59 is shown in FIG. 10, assuming T=1 icosahedral symmetry.

An EM picture of the co-assembled FLA-SAPN-1a and FLA-SAPN-2 proteins at a ratio of 48:12 is shown in FIGS. 4(A)-4(D).

EXAMPLES

Example 1—Cloning

The DNA coding for the nanoparticle constructs were prepared using standard molecular biology procedures. Plasmids containing the DNA coding for the protein sequence LONG-D2-D1-ori (SEQ ID NO: 15)
MGHHHHHHASWRWDGGLVPRGSWQTWNARWDQWSNDWNAWRSDWQAWRDD

WARWRALWMGGRLLLRLEELERRLEELERRLEELERFVAAWTLRVRALER

RLEELERRIEEIARGSGSSARLSDLEANNAVKGESKITVNGAEYTANATG

DKITLAGKTMFIDKTASGVSTLINEDAAAAKKSTANPLASIDSALSKVDA

VRSSLGAIQNRFDSAIGSRNANDGISIAQTTEGALNEINNNLQRVRELSV

QATNGTNSDSDLKSIQDEIQQRLEEIDRVSNQTQFNGVKVLSQDNQMKIQ

VGANDGETITIDLQKIDVKSLGLDGFNVNGPKEATVGDLKSSFKNVTGYD

TYAAGADKYRVDINSGAV was constructed by cloning into the NcoI/EcoRI restriction sites of the basic SAPN expression construct of FIG. 3.

For this construct there is no mixing/co-assembly step of two different constructs. The vaccine immunogen will be generated by covalently attaching the vaccine epitopes such as nicotine to the carrier already incorporating the flagellin derivative, preferentially to the lysine residues.

Figure 2B:
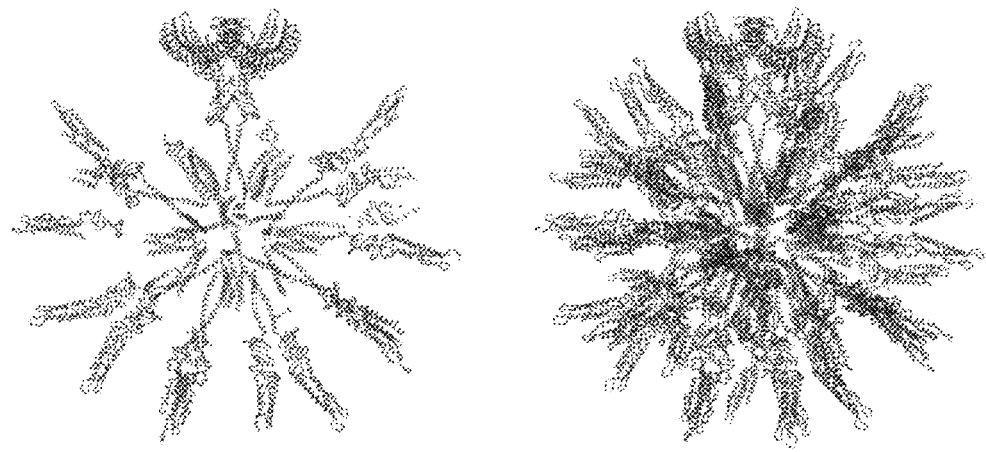

This construct is composed of a pentameric coiled-coil tryptophan zipper (ND1) linked by two glycine residues (GG) to a trimeric de-novo designed coiled-coil (ND2) that contains a panDR binding CD4 epitope string ERFVAAW-TLRVRAL (SEQ ID NO:16). At the N-terminus it contains a His-tag and a thrombin cleavage site (X). This X-ND1-L1-ND2 core architecture is described in detail above. At the C-terminus a flagellin construct (FLA) composed of the D1 and D2 domains of *Salmonella* flagellin from the structure with pdb-code 3V47 (RCSB protein data bank) attached. Residues 348 to 447 spanning portions of the D1 and D2 domains are linked to residues 24 to 214 again spanning portions of D1 and D2 in the opposite direction by means of a single glycine residue. This design attaches the flagellin D1 and D2 molecules to the nanoparticles such that the D1 domain is displayed at the outer surface of the nanoparticle and the TLR5 binding site is exposed to the surface of the nanoparticle (FIG. 2(A)). In contrast to FIG. 2, the de novo designed coiled-coil ND2 is a trimeric coiled-coil.

Example 2—Expression

The plasmids were transformed into *Escherichia coli* BL21 (DE3) cells, which were grown in Luria broth with ampicillin at 37° C. Expression was induced with isopropyl β-D-thiogalactopyranoside. Four hours after induction, cells were removed from 37° C. and harvested by centrifugation at 4,000×g for 15 min. The cell pellet was stored at −20° C. The pellet was thawed on ice and suspended in a lysis buffer consisting of 9 M urea, 100 mM $NaH_2PO_4$, 10 mM Tris pH 8, 20 mM imidazole, and 0.2 mM Tris-2-carboxyethyl phosphine (TCEP).

Alternatively also other cell lines can be used for expression, such as KRX cells. In KRX cells expression can be done with the early auto-induction protocol of KRX cells using 0/N pre-culture at 37 degree with Amp (100 μg/mL) and glucose (0.4%). Diluting the 0/N pre-cultures 1:100 into the expression culture containing Amp (100 μg/mL), glucose (0.05%) and rhamnose (0.1%) at 25° C. for 24 hours. The protein expression level was assessed by sodium dodecyl sulfate polyacrylamide gel electrophoresis (SDS-PAGE) and is shown in FIG. 5. The construct forms monomers, trimers and tetramers even under the denaturing conditions of the SDS-PAGE.

Example 3—Purification

Cells were lysed by sonication and the lysate was cleared by centrifuging at 30,500×g for 45 min. The cleared lysate was incubated with Ni-NTA Agarose Beads (Qiagen, Valencia, Calif., USA) for at least 1 hour. The column was washed with lysis buffer and then a buffer containing 9 M urea, 500 mM $NaH_2PO_4$, 10 mM Tris pH 8, 20 mM imidazole, and 0.2 mM TCEP. The protein was eluted with a pH gradient: 9 M urea, 100 mM $NaH_2PO_4$, 20 mM citrate, 20 mM imidazole, and 0.2 mM TCEP. Subsequent washes were done at pH 6.3, 5.9, and 4.5. Following the pH gradient, a gradient of lysis buffer with increasing imidazole strength was used to further elute the protein. Purity was assessed by sodium dodecyl sulfate polyacrylamide gel electrophoresis (SDS-PAGE) as shown in FIG. 5.

Example 4—Refolding

For refolding the protein was rebuffered to the following conditions: 9 M urea, 20 mM Tris pH 8.5, 50 mM NaCl, 5% glycerol, 2 mM EDTA. For quick refolding of a first screen, 4 μl of a solution with a concentration of 1.8 mg/ml was added to a buffer solution as indicated in Table 3, to a final concentration of 0.05 mg/ml. The solution was then analyzed by negative stain transmission electron microscopy at different resolutions.

TABLE 3

Buffers used for refolding of LONG-D2-D1 (first screen)

| No. | pH | NaCl (mM) | MES (mM) | HEPES (mM) | TRIS (mM) | Glycerol (%) |
|---|---|---|---|---|---|---|
| 1 | 6.5 | 50 | 20 | — | — | 5 |
| 2 | 6.5 | 150 | 20 | — | — | 5 |
| 3 | 7.5 | 50 | — | 20 | — | 5 |
| 4 | 7.5 | 150 | — | 20 | — | 5 |
| 5 | 8.5 | 50 | — | — | 20 | 5 |
| 6 | 8.5 | 150 | — | — | 20 | 5 |

MES = 2-Morpholinoethanesulfonic acid
HEPES = 2-[4-(2-Hydroxyethyl)piperazin-1-yl]ethanesulfonic acid
TRIS = 2-Amino-2-hydroxymethyl-propane-1,3-diol If needed further screens to optimize refolding conditions can be performed with smaller sampling sizes of the pH and the ionic strength. Additionally, excipients such as trehalose, sucrose, arginine, proline or others can be added, or if needed detergents such as cholate, deoxycholate, Tween-80 or others can be added. For LONG-D2-D1-ori no additional optimization of the refolding was needed and the refolding condition was pH 8.5, 50 mM NaCl, 20 mM Tris, 5% glycerol. EM pictures of LONG-D2-D1-ori at different resolution after refolding show nice nanoparticle formation (FIG. 6).

Example 5—TLR5 Pathway Activation Assay I

Agonist activity of LONG-D2-D1-ori on Toll-like receptor 5 (TLR5) was tested using TLR5/SEAPorter HEK 293 cells (IMGENEX, Cat. No. IML-105) and $EC_{50}$ of active LONG-D2-D1-ori was evaluated. The IML-105 cell line was plated in 96-well plates at $5\times10^4$ cells per well for 16 h. Cells were treated with various concentrations (between 0.01 and 1000 ng/ml) of each test sample, positive control (IMGENEX flagellin, Cat. No. IMG-2205) or vehicle control (each corresponding buffer) in duplicate for 24 hours. The cell culture medium from each well was then diluted 1:2 and transferred to 96-well microtiter plates in duplicate, in which serially diluted secreted alkaline phosphatase (SEAP) standards were also added in duplicate. The plates were incubated at 65° C. for 30 min to inactivate any endogenous alkaline phosphatase. The phosphatase substrate was then added to each well and incubated at room temperature for 30 min. The plates were analyzed by reading at 405 nm and dose-responsive activity evaluation and an $EC_{50}$ evaluation prepared (FIG. 7A).

The TLR5 agonist activity was moderately high with a calculated $EC_{50}$ value of 12.59 ng/ml compared to 0.29 ng/ml of the positive control flagellin from *Salmonella typhimurium.*

Example 6—TLR5 Pathway Activation Assay II

Compound of Formula (Ia) Designated T81c-WRW-8RRVRA-D0-D1 (FLJB_SALTY):

```
                                            (SEQ ID NO: 4)
MGHHHHHHASWRWDGGLVPRGSWQTWNARWDQWSNDWNAWRSDWQAWRDD
WARWRALWMGGRLLLRLEELERRLEELERRLEELERRLEELERFVAAWTLRVRALER
RLEELERRIEEIARGMAQVINTNSLSLLTQNNLNKSQSALGTAIERLSSG
LRINSAKDDAAGQAIANRFTANIKGLTQASRNANDGISIAQTTEGALNEI
NNNLQRVRELAVQSANSTNSQSDLDSIQAEITQRLNEIDRVSGQTQFNGV
KVLAQDNTLTIQVGANDGETIDIDLKQINSQTLGLDSLNVHGAPVDPASP
WTENPLQKIDAALAQVDALRSDLGAVQNRFNSAITNLGNTVNNLSEARSR
IEDSDYATEVSNMSRAQILQQAGTSVLAQANQVPQNVLSLLR
```

Compound of Formula (II) Designated T81c-WRW-8RRVRA-T1BT* (FLA-SAPN-2):

```
                                            (SEQ ID NO: 5)
MGHHHHHHASEYLNKIQNSLSTEWSPSSVTGSWQTWNARWDQWSNDWNAW
RSDWQAWRDDWARWRALWMGGRLLLRLEELERRLEELERRLEELERFVAA
```

-continued

```
WTLRVRALERRLEELERRIEEIARGSGDPNANPNVDPNANPNVNANPNAN
PNANP
```

These two co-assembled chains are described in detail above. The ND1-L1-ND2 core architecture, which is the same in both formula (Ia) and (II), i.e. the same as ND3-L2-ND4, is also the same as in Example 1. In chain 1 (formula Ia) the FLA portion is composed of the D0 and D1 domains of flagellin but from a different strain than in Example 1. The substituents Y and Z in chain 2 are the T1 BT* T-cell epitope and a 28 residue long sequence from the NANP repeat region from the CS protein from *Plasmodium falciparum* as B cell epitope.

Cloning, expression, purification and refolding of the two chains are essentially along the protocols described in Examples 1, 2, 3, and 4. The refolding conditions for these co-assembled nanoparticles are pH 7.5, 50 mM NaCl, 20 mM HEPES, 5% glycerol. An EM picture of the co-assembled nanoparticles is shown in FIG. 4A.

Dose-responsive activity evaluation as a TLR5 agonist and an $EC_{50}$ evaluation was performed according to the protocol described in Example 5. The TLR5 agonist activity was very high with a calculated $EC_{50}$ value of only 0.0901 ng/ml compared to 0.29 ng/ml of the positive control flagellin from *Salmonella typhimurium* (FIG. 7B). Hence these nanoparticles induce a very strong TLR5 activation, which is about three-times as strong as native flagellin, even though the flagellin-containing chain is only present at a molar ratio of 12:48. The dose response curve appears to be a bell-shaped curve, hence at higher concentration of flagellin the immune response is decreasing. The optimum concentration is at around 50 ng/ml.

Example 7—TLR5 Pathway Activation Assay III

Compound of Formula (Ia) Designated PD52-2i88-PANDORA-D2-D1-Ori:

```
                                            (SEQ ID NO: 17)
MGHHHHHHASGSWEKWNAKWDEWKNDWNDWRRDWQAWVDDWAYWTLTWKY
GELYSKLAELERRNEELERRLEELARFVAALSMRLAELERRNEELARGSG
SSARLSDLEANNAVRGESKITVNGAEYTANATGDRITLAGRTMFIDRTAS
GVSTLINEDAAAARRSTANPLASIDSALSRVDAVRSSLGAIQNRFDSAIG
SKNANDGISIAQTTEGALNEINNNLQRVRELSVQATNGTNSDSDLRSIQD
EIQQRLEEIDRVSNQTQFNGVKVLSQDNQMKIQVGAKDGETITIDLQKID
VKSLGLDGFNVNGPREATVGDLRSSFRNVTGYDTYAAGADRYRVDINSGA
V
```

Compound of Formula (II) Designated PD52-2i88-PANDORA-Noro:

```
                                            (SEQ ID NO: 18)
MGHHHHHHASGSWEKWNAKWDEWKNDWNDWRRDWQAWVDDWAYWTLTWKY
GELYSKLAELERRNEELERRLEELARFVAALSMRLAELERRNEELARGSG
STVEQKTRPFTLPNLPLSSLSNSRAPLPISSMGISPDNVQSVQFQNGRCT
LDGRLVGTTPVSLSHVAKIRGTSNGTVINLTELDGTPFHPFEGPAPIGFP
```

-continued
DLGGCDWHINMTQFGHSSQTQYDVDTTPDTFVPHLGSIQANGIGSGNYVG

VLSWISPPSHPSGSQVDLWKIPNYGSSITEATHLAPSVYPPGFGEVLVFF

MSKMPGPGAYNLPCLLPQEYISHLASEQAPTVGEAALLHYVDPDTGRNLG

EFKAYPDGFLTCVPNGASSGPQQLPINGVFVFVSWVSRFYQLKPVGTAS

These two co-assembled chains PD52-2i88-PANDORA-D2-D1-ori and PD52-2i88-PANDORA-Noro have the same core architecture in both formula (Ia) and formula (II), i.e. ND1-L1-ND2 is the same as ND3-L2-ND4. In PD52-2i88-PANDORA-D2-D1-ori (formula Ia) the FLA portion is composed of the D2 and D1 domains of flagellin. The oligomerization domain ND2 (or ND4, respectively) is designed to form a dimeric coiled-coil. This is important because the B-cell epitope (Z) as well as the form of flagellin (FLA) are both dimeric proteins. The co-assembly ratio is 5:55.

The substituents Y and Z in PD52-2i88-PANDORA-Noro (formula II) are a His-tag and a 298 residue long sequence from the P-protein of norovirus linked to ND4 by the linker GSGS, respectively. This sequence corresponds to the P2-subdomain of the norovirus Hu/1968/US (Jiang X. et al., Virology 1993; 195(1):51-61) with the corresponding pdb-entry code 1IHM for the X-ray crystal structure. It contains residues 223 to 520 which are the P domain (lacking the 10 C-terminal residues 521-530 because these 10 residues are disordered in the X-ray crystal structure and because they are heavily positively charged) plus 3 amino acids of the C-terminal end of the S domain according to the nomenclature presented by Prasad B. V. V. et al., Science 1999; 286:287-290. The residue threonine 223 was carefully chosen by computer visualization programs to be the attachment point to the noro-SAPN because it is the closest contact between the strands across the 2-fold axis in the crystal structure of the viral capsid.

Cloning, expression, purification and refolding of the two chains are essentially along the protocols described in Examples 1, 2, 3, and 4. The refolding conditions for these co-assembled nanoparticles are pH 6.8, 80 mM NaCl, 20 mM MES, 5% glycerol. An EM picture of the co-assembled (ratio 5:55) nanoparticles is shown in FIG. 4C.

Dose-responsive activity evaluation as a TLR5 agonist and an $EC_{50}$ evaluation was performed according to the protocol described in Example 5. The TLR5 agonist activity was moderately high with a calculated $EC_{50}$ value of 17.66 ng/ml compared to 0.29 ng/ml of the positive control flagellin from Salmonella typhimurium (FIG. 7C).

Example 8—Immunogenicity I

Compound of Formula (Ia) Designated
T81c-8-D0-D1 (Eurogentec 0)

(SEQ ID NO: 19)
MGHHHHHHASWKWDGGLVPRGSWQTWNAKWDQWSNDWNAWRSDWQAWKDD

WARWRALWMGGRLLLRLEELERRLEELAKFVAAWTLKAAAVDLELAALRR

RLEELARGNTNSLSLLTQNNLNKSQSALGTAIERLSSGLRINSAKDDAAG

QAIANRFTANIKGLTQASRNANDGISIAQTTEGALNEINNNLQRVRELAV

QSANSTNSQSDLDSIQAEITQRLNEIDRVSGQTQFNGVKVLAQDNTLTIQ

VGANDGETIDIDLKQINSQTLGLDGGENPLQKIDAALAQVDTLRSDLGAV

QNRFNSAITNLGNTVNNLTSVRSRIEDSDYATEVSNMSRAQILQQAGTSV

LAQANQVPQN

Compound of Formula (II) Designated T81c-8-Pf (SEQ ID NO: 20)
MGHHHHHHASWKWDGGLVPRGSWQTWNAKWDQWSNDWNAWRSDWQAWKDD

WARLRALLMGGRLLLRLEELERRLEELAKFVAAWTLKAAAVDLELAALRR

RLEELARGGSGANANPNANPNANPNANP

These two co-assembled chains are similar as the ones described in Example 6. There is no T1 BT* T-cell epitope in Y and the B cell epitope from the repeat region of the CS protein from Plasmodium falciparum in Z is only 16 residues long. The trimeric coiled-coil (ND2 and ND4) contains the panDR binding epitope PADRE. In chain 1 (formula Ia) the FLA portion is composed of the D0 (residues 6 to 171) and D1 (residues 229 to 312) domains of flagellin but from phase I flagellin middle domain variant C150 Salmonella enterica subsp. enterica serovar Typhimurium, which is again a different strain than in Examples 1 and 6. D0 and D1 are connected by two glycine residues.

Cloning, expression, purification and refolding of the two chains are essentially along the protocols described in Examples 1, 2, 3, and 4. The refolding conditions for this type of co-assembled nanoparticles are pH 8.5, 50 mM NaCl, 20 mM Tris, 5% glycerol. An EM picture of the co-assembled nanoparticles at a ratio of 3:57 is shown in FIG. 4B. Groups of seven C57Bl/6 mice were immunized i.p. with either 10 µg or 1 µg in three injections each two weeks apart. The immunogens were either T81c-8-Pf (formula II) alone or the co-assembly of T81c-8-D0-D1 (formula Ia) and T81c-8-Pf (formula II) at two different co-assembly ratios of 3:57 and 9:51. In other words—assuming T1-icosahedral symmetry of the nanoparticles—there were three different immunogens that contain either zero or three or nine D0-D1 molecules per nanoparticle. The antibody titer after the third injection has been determined by ELISA and is shown in FIG. 8A. There appears to be a saturation of the immune response, with 1 µg at a co-assembly ratio of 3:57 (corresponding to a total of roughly 20 ng flagellin) increasing the antibody titer by a factor of about nine compared to the nanoparticle without D0-D1 domains. The higher dose of 10 µg at a co-assembly ratio of 9:51 (corresponding to a total of roughly 2 µg flagellin) in fact reduces the immune response somewhat compared to the nanoparticle without D0-D1 domains.

Example 9—Immunogenicity II

Compound of Formula (Ia) Designated DIM-D0-D1
(Eurogentec 1)

(SEQ ID NO: 21)
MGHHHHHHASGSWEEWNARWDEWENDWNDWREDWQAWRDDWARWRATWMG

GRLLSRLERLERRNEELRRLLQLLRNRLERLAQFVRALSMQNAELERRLE

ELARGMAQVINTNSLSLLTQNNLNKSQSALGTAIERLSSGLRINSAKDDA

-continued
AGQAIANRFTANIKGLTQASRNANDGISIAQTTEGALNEINNNLQRVREL

AVQSANSTNSQSDLDSIQAEITQRLNEIDRVSGQTQFNGVKVLAQDNTLT

IQVGANDGETIDIDLKQINSQTLGLDSLNVHGAPVDPASPWTENPLQKID

AALAQVDALRSDLGAVQNRFNSAITNLGNTVNNLSEARSRIEDSDYATEV

SNMSRAQILQQAGTSVLAQANQVPQNVLSLLR

Compound of Formula (II) Designated
DIM-D2-D1-Tip3_NIC-Pept (SEQ ID NO: 22)
MGHHHHHHASGSWEEWNARWDEWENDWNDWREDWQAWRDDWARWRATWMG

GRLLSRLERLERRNEELRRLLQLLRNRLERLAQFVRALSMQNAELERRLE

ELARGSGSSARLSDLEANNAVRGESKITVNGAEYTANATGDRITLAGRTM

FIDRTASGVSTLINEDAAAARRSTANPLASIDSALSRVDAVRSSLGAIQN

RFDSAKAKKKDGKDDKDSKNANDGISIAQTTEGALNEINNNLQRVRELSV

QATNGTNSDSDLRSIQDEIQQRLEEIDRVSNQTQFNGVKVLSQDNQMKIQ

VGAKDGETITIDLQKIDVKSLGLDGFNVNGPREATVGDLRSSFRNVTGYD

TYAAGADRYRVDINSGAV

According to Example 5 and Example 6 the flagellin derivative seems to be more immunogenic in its D0-D1 form than in its D2-D1 form. Therefore the D0-D1 form can be used as the TLR5 agonist to increase the immunogenicity of an immunogen that carries the D2-D1 form of flagellin. Hence in this example the sequence D0-D1

(SEQ ID NO: 23)
MAQVINTNSLSLLTQNNLNKSQSALGTAIERLSSGLRINSAKDDAAGQAI

ANRFTANIKGLTQASRNANDGISIAQTTEGALNEINNNLQRVRELAVQSA

NSTNSQSDLDSIQAEITQRLNEIDRVSGQTQFNGVKVLAQDNTLTIQVGA

NDGETIDIDLKQINSQTLGLDSLNVHGAPVDPASPWTENPLQKIDAALAQ

VDALRSDLGAVQNRFNSAITNLGNTVNNLSEARSRIEDSDYATEVSNMSR

AQILQQAGTSVLAQANQVPQNVLSLLR corresponds to "FLA" in formula (Ia), while the sequence D2-D1-tip3

(SEQ ID NO: 24)
SARLSDLEANNAVRGESKITVNGAEYTANATGDRITLAGRTMFIDRTASG

VSTLINEDAAAARRSTANPLASIDSALSRVDAVRSSLGAIQNRFDSAKAK

KKDGKDDKDSKNANDGISIAQTTEGALNEINNNLQRVRELSVQATNGTNS

DSDLRSIQDEIQQRLEEIDRVSNQTQFNGVKVLSQDNQMKIQVGAKDGET

ITIDLQKIDVKSLGLDGFNVNGPREATVGDLRSSFRNVTGYDTYAAGADR

YRVDINSGAV corresponds to "Z" in formula (II). This sequence "Z" in D2-D1-tip3 is a modification of flagellin in which the D2 domain is combined with the D1 domain of flagellin as described above. In addition, the protein scaffold of D2-D1-tip3 is used as a carrier for the display of the antigen nicotine. To allow covalent coupling of activated nicotine to the protein scaffold, the lysine side chains that are not surface exposed are mutated to arginines, while the arginines that are surface exposed are mutated to lysines. Upon covalent attachment of activated nicotine to the primary amines of the protein sequence, the nicotine is then displayed at the surface of the nanoparticle. Furthermore, to display the nicotine molecules at the outermost surface of the nanoparticles, the D2-D1 protein carries as so-called "tip3" sequence KAKKKDGKDDKD (SEQ ID NO:25) at the most exposed portion of the molecule (FIG. 2A) that contains a high density of lysines, hence covalent coupling of nicotine to the lysine side chains will provide a high-density display of nicotine molecules at the surface of the nanoparticle.

The cores of DIM-D0-D1 and DIM-D2-D1-tip3_NIC-pept (i.e. ND1-L1-ND2 and ND3-L2-ND4) are identical and in particular the oligomerization domains ND2 and ND4, respectively, are designed to form dimeric coiled-coils. This allows displaying the flagellin molecule (in either form) as a dimer, ready to interact with the dimeric TL5-receptor (FIG. 2B).

Cloning, expression, purification and refolding of the two chains are essentially along the protocols described in Examples 1, 2, 3, and 4. The refolding conditions for this type of co-assembled nanoparticles are pH 7.0, 50 mM NaCl, 20 mM HEPES, 5% glycerol. An EM picture of the co-assembled nanoparticles at a ratio of 5:55 is shown in FIG. 4D.

Groups of seven C57Bl/6 mice were immunized i.p. with 10 μg in three injections each two weeks apart. The immunogens were either the co-assembly of DIM-D0-D1 (formula Ia) and DIM-D2-D1-tip3_NIC-pept (formula II) at the co-assembly ratio of 5:55 or the standard carrier KLH (keyhole limpet hemocyanin) to which the same activated nicotine molecule was attached. KLH is a large, multisubunit, oxygen-carrying, metalloprotein found in the hemolymph of the giant keyhole limpet and frequently used as a carrier for antigens in immunization experiments. The antibody titer after the third injection has been determined by ELISA and is shown in FIG. 8B. The antibody titer of this type of nanoparticle immunogen with the TLR5-agonist is significantly increased compared to the titer of the standard carrier KLH displaying the same antigen (nicotine) on its surface.

Example 10—Immunogenicity III

Compound of formula (Ia) designated DEDDL:

(SEQ ID NO: 26)
MGDKHHHHHHKDGSDKGSWEEWNARWDEWENDWNDWREDWQAWRDDWARW

RATWMGGRLLSRLERLERRNEELRRLLQLLRNRLERLAQFVRALSMQNAE

LERRLEELARGMAQVINTNSLSLLTQNNLNRSQSALGTAIERLSSGLRIN

SARDDAAGQAIANRFTANIRGLTQASRNANDGISIAQTTEGALNEINNNL

QRVRELAVQSANSTNSQSDLDSIQAEITQRLNEIDRVSGQTQFNGVRVLA

QDNTLTIQVGANDGETIDIDLRQINSQTLGLDQLNVQQKYKDGDKGDDKT

ENPLQRIDAALAQVDALRSDLGAVQNRFNSAITNLGNTVNNLSEARSRIE

DSDYATEVSNMSRAQILQQAGTSVLAQANQVPQNVLSLLR

This nanoparticle protein chain contains as "FLA" a modified D0-D1 domain from phase I flagellin middle domain variant C150 *Salmonella enterica* subsp. *enterica* serovar *Typhimurium*, as in Example 8. All lysine residues within this sequence are replaced by arginine. The D0 and D1 domains are connected by the amino acid sequence KYKDGDKGDDK (SEQ ID NO:1), which contains four lysines as coupling sites for covalent attachment of molecules.

The trimeric coiled-coil (ND2) contains the panDR binding sequence ELRRLLQLLRNRLERLAQFVRALSMQNA (SEQ ID NO:27). The substituent "X" contains a his-tag of six amino acids and three lysine residues roughly evenly distributed throughout the sequence for covalent attachment of molecules. Also the N-terminus is suitable for covalent attachment, for example by N-hydroxysuccinimide ester (NHS) chemistry.

Cloning, expression and purification of the protein chain are essentially along the protocols described in Examples 1, 2, and 3.

Prior to buffer exchange for the coupling reaction, the pooled elution fractions from the affinity purification were incubated with 5 mM EDTA at least for an hour to chelate any possible leached nickel ions. Then the buffer was exchanged using a HiPrep 26/10 desalting column. The column was equilibrated with 5 column volumes of the following coupling buffer: 6 M guanidium hydrochloride, 150 mM NaCl, 20 mM HEPES pH 7.2, followed by binding of the sample to the column. The elution step was performed with 2 column volumes of coupling buffer.

Coupling of NHS-nicotine (nicotinic acid N-hydroxysuccinimide ester) was done in a molar ratio of 1:50 (DEDDL: NHS-nicotine) with 11.1 mg of protein (2.5 mL volume) corresponding to 0.24 μmol of protein. The NHS-nicotine (5 mg) was dissolved in 150 μL of 100% DMSO corresponding to 12.8 μmol. For 50-fold molar excess of NHS-nicotine 141 μL of this NHS-nicotine solution corresponding to 12 μmol was added to the protein. The coupling reaction was incubated for 3 hours in the dark (covered with aluminum foil) and stirring with magnetic stirrer.

In a next buffer exchange step to get rid of the uncoupled NHS-nicotine and to buffer exchange to the pre-refolding buffer, a PD minitrap G-25 prepacked column was used to rebuffer into the following conditions: 8 M urea, 20 mM Tris pH 8.5, 150 mM NaCl and 10% trehalose.

Refolding of the protein chain was essentially along the protocol described in Example 4. In particular 8 mg of coupled Nic-DEDDL protein (DEDDL protein coupled to nicotine, 2.4 mL of protein solution of 3.35 mg/mL) was added drop wise to 158.4 mL of refolding buffer (20 mM HEPES pH 7.0, 150 mM NaCl, 10% trehalose) while stirring. The final protein concentration aimed at was 0.05 mg/mL. Refolding reaction was done for a total time of 10 minutes. Refolded Nic-DEDDL nanoparticles are shown in FIG. 9.

Groups of three C57Bl/6 mice were immunized s.c. with either 10 μg of Nic-DEDDL or 10 μg of Nic-KLH (nicotine coupled to keyhole limpet hemocyanin) as a positive control in three injections each one week apart. The antibody titer at day 0 (i.e. before the first injection) and then one week after each injection (day 7, 14 and 21) has been determined by ELISA and is shown in FIG. 10. These experiments reveal that Nic-DEDDL is highly immunogenic with a >30-fold better antibody induction compared to Nic-KLH. Peak values after only 3 immunizations are at titers of close to 163840.

The invention claimed is:

1. A self-assembling protein nanoparticle consisting of aggregates of a multitude of building blocks of formula (Ia) or (Ib)

X-ND1-L1-ND2-FLA    (Ia)

or

FLA-ND1-L1-ND2-X    (Ib), consisting of a continuous chain comprising a protein oligomerization domain ND1, a linker L1, a protein oligomerization domain ND2, FLA, and a further substituent X, wherein ND1 is a protein that forms oligomers $(ND1)_m$ of m subunits ND1, ND2 is a protein that forms oligomers $(ND2)_n$ of n subunits ND2, m and n each is a figure between 2 and 10, with the proviso that m is not equal to n and not a multiple of n, and n is not a multiple of m, L1 is a bond or a short flexible linker, FLA is flagellin, or a derivative of flagellin lacking parts of the flagellin amino acid sequence but at least containing the TLR5 binding domain D1, and wherein the lacking parts are (a) replaced by a flexible linker segment of 1 to 20 amino acids joining two ends of the flagellin amino acid sequence or (b) are replaced by a fully folded protein antigen;

X is absent or a peptide or protein sequence comprising 1 to 1000 amino acids, optionally co-assembled with a multitude of building blocks of the formula (II)

Y-ND3-L2-ND4-Z    (II), consisting of a continuous chain comprising a protein oligomerization domain ND3, a linker L2, a protein oligomerization domain ND4, and further substituents Y and Z, wherein ND3 is a protein that forms oligomers $(ND3)_y$ of y subunits ND3, ND4 is a protein that forms oligomers $(ND4)_z$ of z subunits ND4, y and z each is a figure between 2 and 10, with the proviso that y is not equal to z and not a multiple of z, and z is not a multiple of y, and wherein either ND3 is identical to ND1, or ND4 is identical to ND2 or both ND3 and ND4 are identical to ND1 and ND2, respectively, L2 is a bond or a short flexible linker that may be different from L1 or identical to L1, and Y and Z are, independently of each other, absent or a peptide or protein sequence comprising 1 to 1000 amino acids.

2. The protein nanoparticle according to claim 1 consisting of aggregates of a multitude of building blocks of formula (Ia) or (Ib)

X-ND1-L1-ND2-FLA    (Ia)

or

FLA-ND1-L1-ND2-X    (Ib), co-assembled with a multitude of building blocks of the formula (II)

Y-ND3-L2-ND4-Z    (II).

3. The protein nanoparticle according to claim 1 in which at least one of ND1 and ND2 and at least one of ND3 and ND4 is a coiled-coil.

4. The protein nanoparticle according to claim 1 wherein at least one of X, Y and Z is an antigen of interest.

5. The protein nanoparticle according to claim 1 wherein the flagellin derivative is lacking the D2 and D3 domains of flagellin.

6. The protein nanoparticle according to claim 1 wherein the flagellin derivative comprises an antigen of interest.

7. The protein nanoparticle according to claim 1 wherein n in a building block of formula (Ia) or m in a building block of formula (Ib) is 2.

8. The protein nanoparticle according of claim 7 wherein FLA is connected at the D2 part of flagellin to the oligomerization domain ND2 in formula (Ia), wherein n is 2, or to the oligomerization domain ND1 in formula (Ib), wherein m is 2.

9. The protein nanoparticle according to claim 1 wherein at least one of ND1, ND2, ND3 and ND4 is a coiled-coil.

10. The protein nanoparticle according to claim 1 wherein at least one of ND1, ND2, ND3 and ND4 is the trimerization domain of the bacteriophage T4 protein fibritin.

11. A composition comprising a protein nanoparticle according to claim 1.

12. A monomeric building block of formula (Ia) or (Ib)

X-ND1-L1-ND2-FLA    (Ia)

or

FLA-ND1-L1-ND2-X    (Ib), consisting of a continuous chain comprising a protein oligomerization domain ND1, a linker L1, a protein oligomerization domain ND2, FLA, and a further substituent X, wherein ND1 is a protein that forms oligomers $(ND1)_m$ of m subunits ND1, ND2 is a protein that forms oligomers $(ND2)_n$ of n subunits ND2, m and n each is a figure between 2 and 10, with the proviso that m is not equal to n and not a multiple of n, and n is not a multiple of m, L1 is a bond or a short flexible linker, FLA is flagellin, or a derivative of flagellin lacking parts of the flagellin amino acid sequence but at least containing the TLR5 binding domain D1, and wherein the lacking parts are (a) replaced by a flexible linker segment of 1 to 20 amino acids joining two ends of the flagellin amino acid sequence or (b) are replaced by a fully folded protein antigen; and X is absent or a peptide or protein sequence comprising 1 to 1000 amino acids.

13. A method of vaccinating a human or non-human animal, which comprises administering an effective amount of a protein nanoparticle according to claim 1 to a subject in need of such vaccination.

* * * * *